United States Patent
Chen et al.

(10) Patent No.: US 10,863,756 B2
(45) Date of Patent: *Dec. 15, 2020

(54) METHOD OF PREVENTING OBESITY AND CARDIOVASCULAR PROBLEMS IN POULTRY

(71) Applicant: DSM IP Assets B.V., Heerlen (NL)

(72) Inventors: Shuen Ei Chen, Kaiseraugst (CH); Thau Kiong Chung, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/542,143

(22) PCT Filed: Jan. 15, 2016

(86) PCT No.: PCT/EP2016/050751
§ 371 (c)(1),
(2) Date: Jul. 7, 2017

(87) PCT Pub. No.: WO2016/113383
PCT Pub. Date: Jul. 21, 2016

(65) Prior Publication Data
US 2018/0264009 A1    Sep. 20, 2018

Related U.S. Application Data

(60) Provisional application No. 62/103,769, filed on Jan. 15, 2015.

(30) Foreign Application Priority Data

May 8, 2015  (EP) .................... 15166937

(51) Int. Cl.

| | | |
|---|---|---|
| A23K 20/174 | (2016.01) | |
| A23K 20/179 | (2016.01) | |
| A23K 50/10 | (2016.01) | |
| A23K 50/75 | (2016.01) | |
| A61K 9/00 | (2006.01) | |
| A61K 31/122 | (2006.01) | |
| A61K 31/197 | (2006.01) | |
| A61K 31/355 | (2006.01) | |
| A61K 31/375 | (2006.01) | |
| A61K 31/4188 | (2006.01) | |
| A61K 31/455 | (2006.01) | |
| A61K 31/519 | (2006.01) | |
| A61K 31/525 | (2006.01) | |
| A61K 31/593 | (2006.01) | |
| A61K 31/675 | (2006.01) | |
| A61K 33/04 | (2006.01) | |
| A61K 33/26 | (2006.01) | |
| A61K 33/32 | (2006.01) | |
| A61K 33/34 | (2006.01) | |
| A23K 50/42 | (2016.01) | |
| A23K 50/48 | (2016.01) | |
| A61P 3/08 | (2006.01) | |
| A61P 39/00 | (2006.01) | |
| A61P 9/00 | (2006.01) | |
| A61P 3/06 | (2006.01) | |
| A61K 31/015 | (2006.01) | |
| A23K 20/20 | (2016.01) | |
| A61P 15/00 | (2006.01) | |
| A61P 15/08 | (2006.01) | |

(52) U.S. Cl.
CPC .......... *A23K 20/174* (2016.05); *A23K 20/179* (2016.05); *A23K 20/30* (2016.05); *A23K 50/10* (2016.05); *A23K 50/42* (2016.05); *A23K 50/48* (2016.05); *A23K 50/75* (2016.05); *A61K 9/0056* (2013.01); *A61K 31/015* (2013.01); *A61K 31/122* (2013.01); *A61K 31/197* (2013.01); *A61K 31/355* (2013.01); *A61K 31/375* (2013.01); *A61K 31/4188* (2013.01); *A61K 31/455* (2013.01); *A61K 31/519* (2013.01); *A61K 31/525* (2013.01); *A61K 31/593* (2013.01); *A61K 31/675* (2013.01); *A61K 33/04* (2013.01); *A61K 33/26* (2013.01); *A61K 33/32* (2013.01); *A61K 33/34* (2013.01); *A61P 3/06* (2018.01); *A61P 3/08* (2018.01); *A61P 9/00* (2018.01); *A61P 15/00* (2018.01); *A61P 15/08* (2018.01); *A61P 39/00* (2018.01)

(58) Field of Classification Search
None
See application file for complete search history.

(56) References Cited

U.S. PATENT DOCUMENTS

| | | |
|---|---|---|
| 6,034,075 A | 3/2000 | Thys-Jacobs |
| 7,632,518 B2 | 12/2009 | Tritsch et al. |

(Continued)

FOREIGN PATENT DOCUMENTS

| | | |
|---|---|---|
| CN | 1615139 | 5/2005 |
| CN | 1720030 | 1/2006 |

(Continued)

OTHER PUBLICATIONS

Vanga, S.R.; Good, M.; Howard, P.A.; Vacek, J.L. Role of Vitamin D in cardiovascular Health. The American Journal of Cardiology, pp. 788-805. (Year: 2010).*

(Continued)

*Primary Examiner* — Jessica Worsham
(74) *Attorney, Agent, or Firm* — Nixon & Vanderhye P.C.

(57) ABSTRACT

Provided is a feed for ameliorating weight gain in poultry comprising 25-hydroxy vitamin D, canthaxanthin, Vitamin E and Vitamin C. Animals fed this composition gained weight, but did not become obese, nor did they experience adverse effects associated with hyperphagia related obesity. This feed also provides numerous cardiovascular benefits.

2 Claims, 33 Drawing Sheets

(56) References Cited

U.S. PATENT DOCUMENTS

| | | |
|---|---|---|
| 2003/0125229 A1 | 7/2003 | Rodriguez |
| 2006/0034912 A1 | 2/2006 | Giordano et al. |
| 2006/0069151 A1 | 3/2006 | Barella et al. |
| 2010/0098779 A1 | 4/2010 | Balzer et al. |
| 2010/0112162 A1 | 5/2010 | Tritsch et al. |
| 2013/0011377 A1 | 1/2013 | Perrin et al. |
| 2013/0281533 A1 | 10/2013 | Yamka et al. |

FOREIGN PATENT DOCUMENTS

| | | |
|---|---|---|
| CN | 102215700 | 10/2011 |
| JP | 48-67061 | 9/1973 |
| JP | 9-294544 | 11/1997 |
| JP | H11-35469 | 2/1999 |
| JP | 2005-519894 | 7/2005 |
| JP | 2006-510647 | 3/2006 |
| JP | 2008-106023 | 5/2008 |
| JP | 2009-27941 | 2/2009 |
| JP | 2011-511826 | 4/2011 |
| JP | 2011-511827 | 4/2011 |
| JP | 2012-509253 | 4/2012 |
| SU | 1748784 | 7/1992 |
| WO | WO 2008/031602 | 3/2008 |
| WO | WO 2010/057811 | 5/2010 |
| WO | WO 2014/191153 | 12/2014 |
| WO | WO 2014/202433 | 12/2014 |

OTHER PUBLICATIONS

International Search Report for PCT/EP2016/050751, dated Apr. 26, 2016, 3 pages.
Villar-Patinño et al., "Effects of Dietary Supplementation with Vitamin C or Vitamin E on Cardiac Lipid Peroxidation and Growth Performance in Broilers at Risk of Developing Ascites Syndrome", American Journal of Veterinary Research, American Veterinary Medicine Association, US, vol. 63, No. 5, May 1, 2002, pp. 673-676.
About DSM, "DSM Vitamin Supplementation Guidelines 2011 Health @Bullet Nutrition @Bullet Materials for domestic animals Guidelines for Optimum Vitamin Nutrition DSM vitamin supplementation guidelines are designed to provide Optimum Vitamin Nutrition under typical industry practices. Optimum Vitamin Nutrition co", Aug. 11, 2014, 14 pages.
Amengual et al., "Beta-Carotene Reduces Body Adiposity of Mice via BCMO1", PLoS ONE, vol. 6, No. 6, Jun. 1, 2011, 14 pages.
Bhuvaneswari et al., "Astaxanthin restricts weight gain, promotes insulin sensitivity and curtails fatty liver disease in mice fed an obesity-promoting diet", Process Biochemistry, vol. 45, No. 8, Aug. 1, 2010, pp. 1406-1414.
Buryakov et al., "Feeding of broiler chicks—involves addn. of sodium ascorbate to basic feed mix to increase live wt. gain", WPI / Thomson, vol. 1993, No. 27, Jul. 23, 1992.
Muscogiuri et al., "Low Levels of 25(OH) D and insulin-resistance: 2 unrelated features or a cause-effect in PCOS?" Clinical Nutrition, vol. 31, No. 4, pp. 476-480.
Ruschkowski et al., Ionic and Endocrine Characteristics of Reproductive Failure in Calcium-Defficient and Vitamin D-Deficient Laying Hens, Poultry Science, vol. 71, Issue 10, pp. 1722-1732.
Stankiewicz et al., "Macro-elements composition of cystic and follicular fluid in the ovaries and their relationship to peripheral blood concentration in sows", Acta Veterinaria-Beograd, 65(2), 2015, pp. 217-225.
Walzem et al., "Obesity-Induced Dysfunctions in Female Reproduction: Lessons from Birds and Mammals", Advances in Nutrition: An International Review Journal, vol. 5, No. 2, Mar. 1, 2014, pp. 199-206.
International Search Report for PCT/EP2016/050749 dated May 23, 2016, 3 pages.
International Search Report for PCT/EP2016/050753 dated Apr. 20, 2016, 3 pages.
International Search Report for PCT/EP2016/050755 dated Apr. 21, 2016, 3 pages.
International Search Report for PCT/EP2016/050759 dated Apr. 26, 2016, 4 pages.
International Search Report for PCT/EP2016/050762 dated Apr. 29, 2016, 5 pages.
International Search Report for PCT/EP2016/050764 dated Apr. 19, 2016, 3 pages.
Office action for U.S. Appl. No. 15/541,852 dated May 30, 2018 (12 pages).
Office action for U.S. Appl. No. 15/542,091 dated Aug. 10, 2018 (17 pages).
Office action for U.S. Appl. No. 15/542,187 dated Jul. 25, 2018 (14 pages).
Office action for U.S. Appl. No. 15/542,500 dated Sep. 10, 2018 (16 pages).
Office action for U.S. Appl. No. 15/542,509 dated Sep. 7, 2018 (16 pages).
Official Action, Colombia Appln. No. NC2017/0007058, dated Aug. 17, 2018 (English Translation).
Written Opinion of the ISA for PCT/EP2016/050749 dated May 23, 2016, 8 pages.
Written Opinion of the ISA for PCT/EP2016/050751 dated Apr. 26, 2016, 6 pages.
Written Opinion of the ISA for PCT/EP2016/050753 dated Apr. 20, 2016, 6 pages.
Written Opinion of the ISA for PCT/EP2016/050755 dated Apr. 21, 2016, 8 pages.
Written Opinion of the ISA for PCT/EP2016/050759 dated Apr. 26, 2016, 8 pages.
Written Opinion of the ISA for PCT/EP2016/050762 dated Apr. 29, 2016, 7 pages.
Written Opinion of the ISA for PCT/EP2016/050764 dated Apr. 19, 2016, 8 pages.
Franks, S. "Adult polycystic ovary syndrome begins in childhood" *Best Practice & Research Clinical Endocrinology and Metabolism*, 16 (2), 263-272 Year: 2002).
Franks, S. "Polycystic Ovary Syndrome" NEJM, 333 (13), 853-861 (Year: 1995).
Garcia et al., "Use of Vitamin $D_3$ and Its Metabolites in Broiler Chicken Feed on Performance, Bone Parameters and Meat Quality" *Asian-Aust. J. Anim. Sci*, vol. 26, No. 3: 408-415 (Mar. 2013).
Merriam-Webster Medical Dictionary, Medical Definition of *supraphysiological* https://www.meriam-webster.com/medical/supraphysiological, retrieved on May 19, 2019.
*Nutrient Requirements of Poultry: Ninth Revised Edition*, The National Academics of Sciences Engineering Medicine, 176 pages (1994).
Rosenfield, R.L. et al. "Dysregulation of cytochrome P450c17α as the cause of polycystic ovarian syndrome" Fertilit and Sterilit 1990, 53 (5), 785-791 Year: 1990.
Office Action issued in U.S. Appl. No. 15/541,793 dated Mar. 25, 2019.
Office Action issued in U.S. Appl. No. 15/541,852 dated Dec. 27, 2018.
Office Action issued in U.S. Appl. No. 15/542,091 dated May 23, 2019.
Office Action issued in U.S. Appl. No. 15/542,500 dated May 23, 2019.
Office Action issued in U.S. Appl. No. 15/542,187 dated May 13, 2019.
Office Action issued in U.S. Appl. No. 15/542,509 dated May 23, 2019.
Office Action issued in JP Appln. No. 2017-534244 dated Jul. 23, 2019 (w/ translation).
Office Action issued in JP Appln. No. P2017-530279 dated Sep. 3, 2019 (translation).
Office Action issued in U.S. Appl. No. 15/541,793 dated Sep. 17, 2019.
Lui et al., "A short-term supranutritional vitamin E supplementation alleviated respiratory alkalosis but did not reduce oxidative stress in head stressed pigs" *Asian-Ausralas J Anim Sci*, vol. 31, No. 2: 263-269 (Feb. 2018).

(56) References Cited

OTHER PUBLICATIONS

Nielsen et al., "Elimination of Ascorbic Acid After High-Dose Infusion in Prostate Cancer Patients: A Pharmacokinetic Evaluation" *Basic & Clinical Pharmacology & Toxicology*, vol. 116: 343-348 (2015).

Quaranta et al., "The effects of 'supra-physiological' vitamin $B_{12}$ administration on temporary threshold shift" *International Journal of Audiology*, vol. 43: 162-165 (2004).

Vollbracht et al., "Commentary: Supraphysiological vitamin B12 serum concentrations without supplementation: the pitfalls of interpretation" *QJM: An International Journal of Medicine*, vol. 0, No. 0: 1-2 (2019).

Witmer et al., "Direct spectrophotometric measurement of supraphysiological levels of ascorbate in plasma" *Redox Biology*, vol. 8: 298-304 (2016).

Cheng et al., "The coupling of epidermal growth factor receptor down regulations and cell cycle arrest in growth suppression of ovarian cancer cells by 1α, 25-dihydroxyvitamin $D_3$" *Modern Oncology*, vol. 18, No. 2: 229-232 (Feb. 2010).

Madar et al., "Effect of vitamin $D_3$ supplementation on glycated hemoglobin (HbA1c) fructosamine, serum lipids, and body mass index: a randomized, double-blinded, placebo-controlled trial among healthy immigrants living in Norway" *BMJ Open Diabetes Research & Care*, vol. 2: e000026, pp. 1-8 (2014).

Yan et al., "Preliminary study on the relationship between vitamin D and polycystic ovary syndrome" *Prog Obstet Gynecol*, vol. 19, No. 11 (Nov. 2010)—(w/ Abstract).

\* cited by examiner

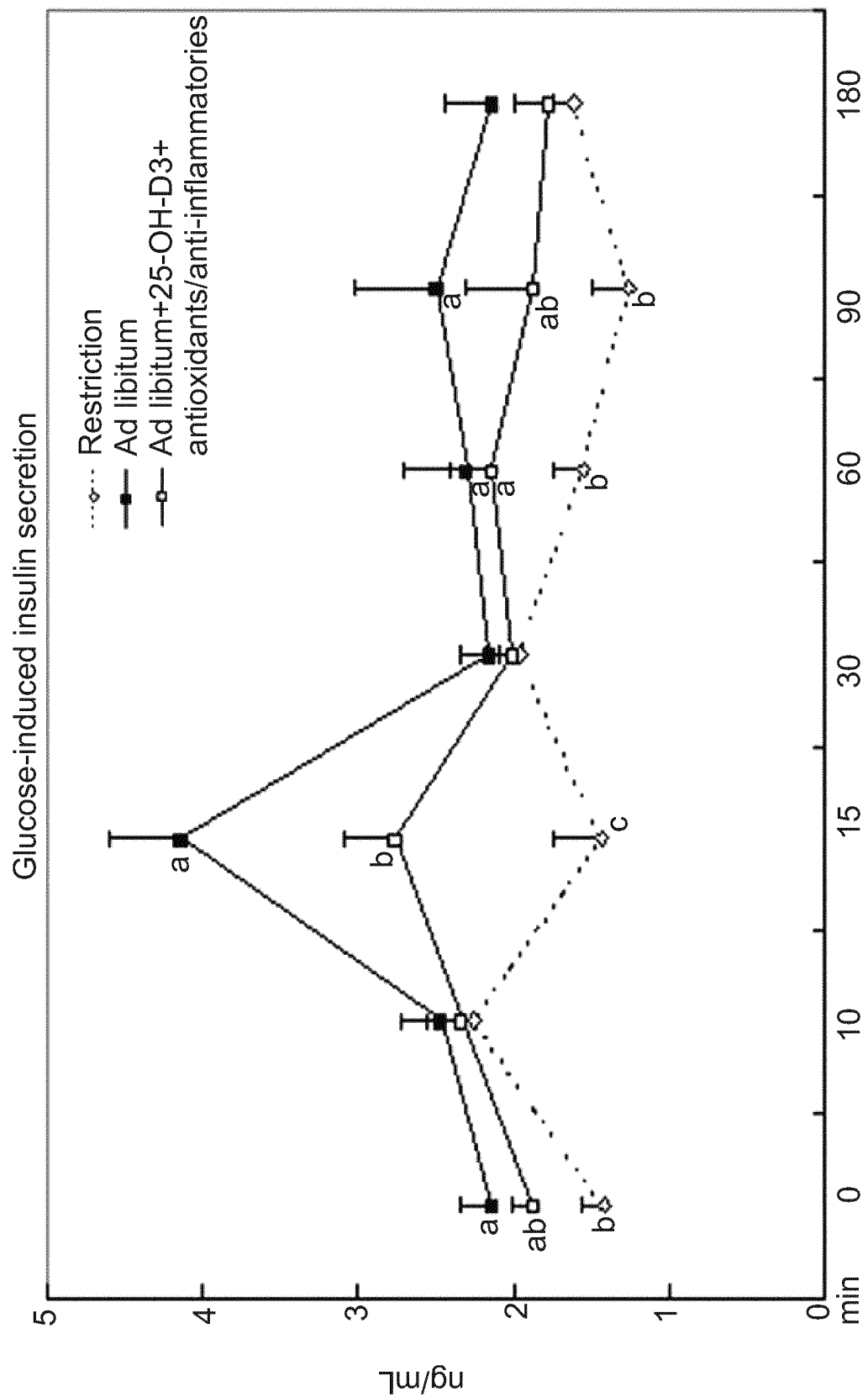
Fig. 1, ctd.

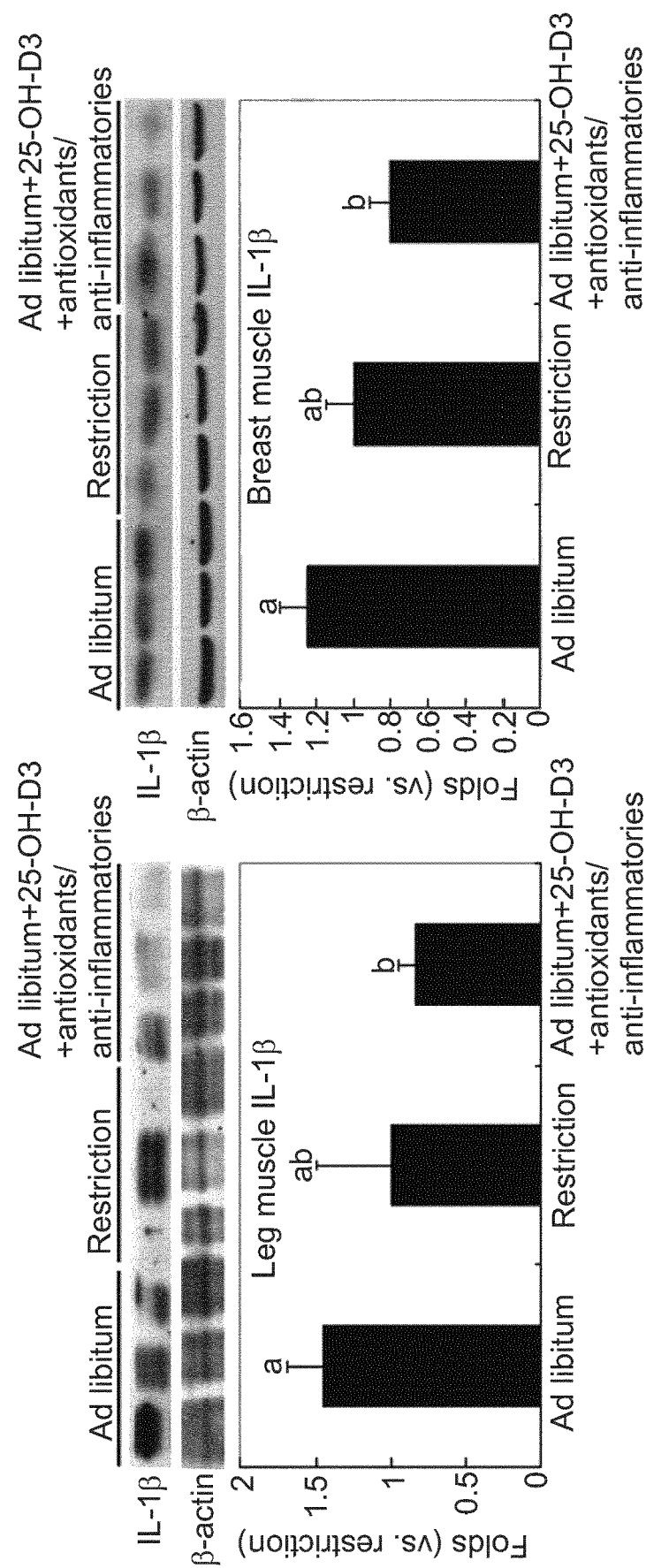
Fig. 2, ctd.

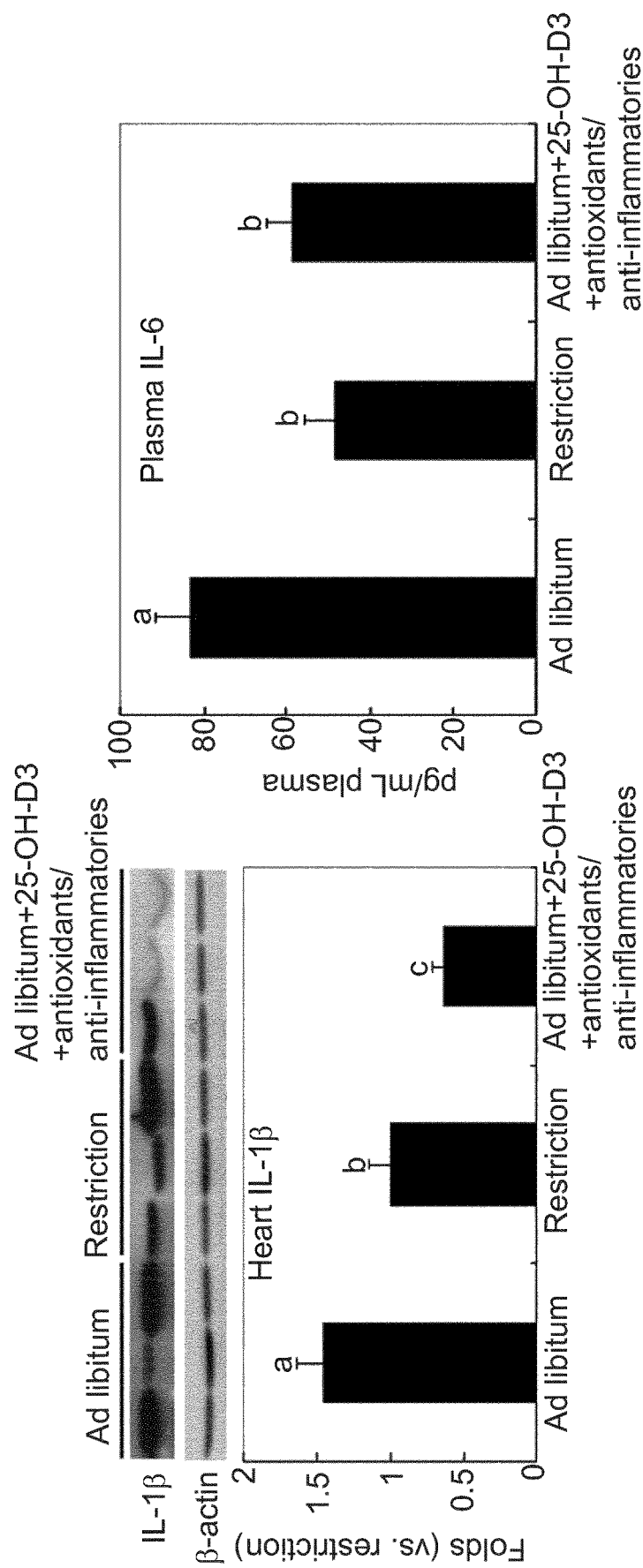
Fig. 2, ctd.

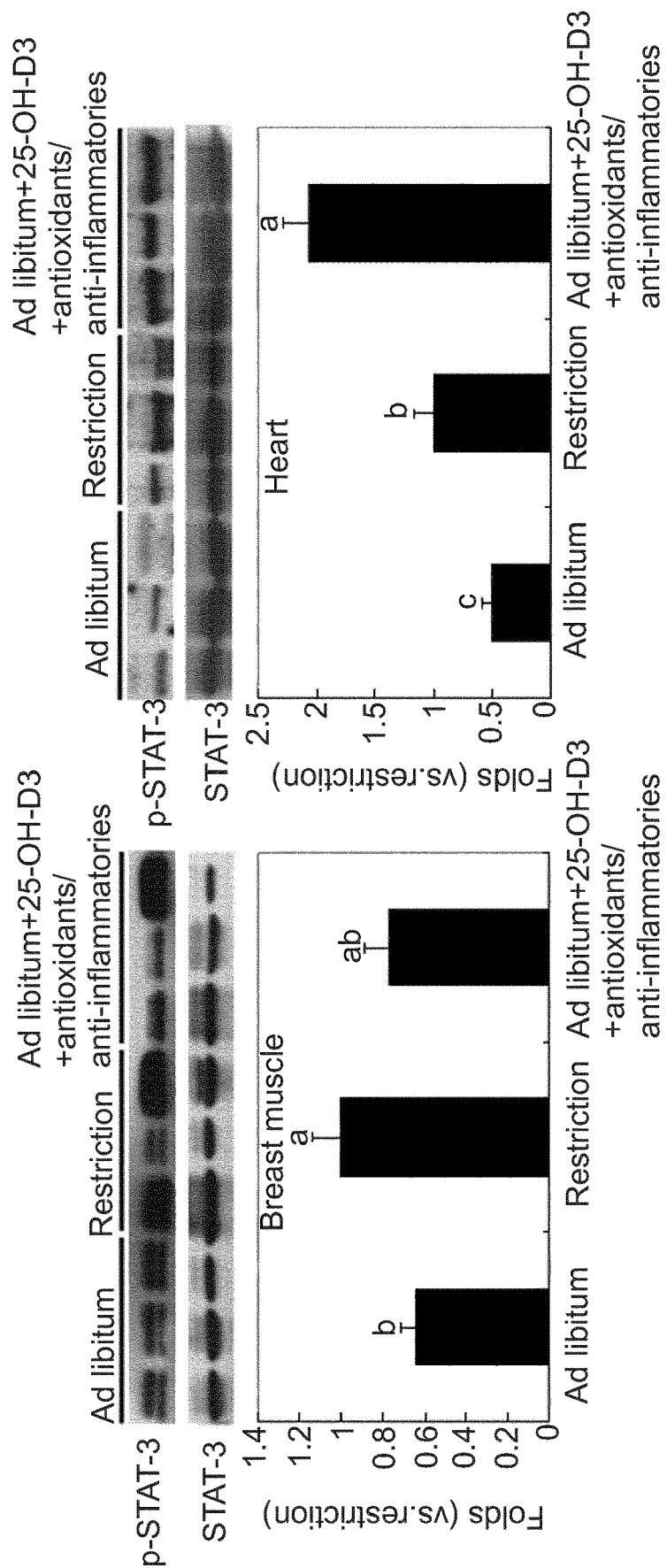
Fig. 3, cdt.

Cardiac ventricle dilation

Normal ventricle

Transudate within pericardium

Transudate within pericardium

Normal pericardium

Normal pericardium

Ascites (transudate in the abdominal cavity)

Normal morphology of abdominal cavity

Ovarian tumor-like morphology

Degenerated ovarian morphology

Normal ovarian morphology dilated heart

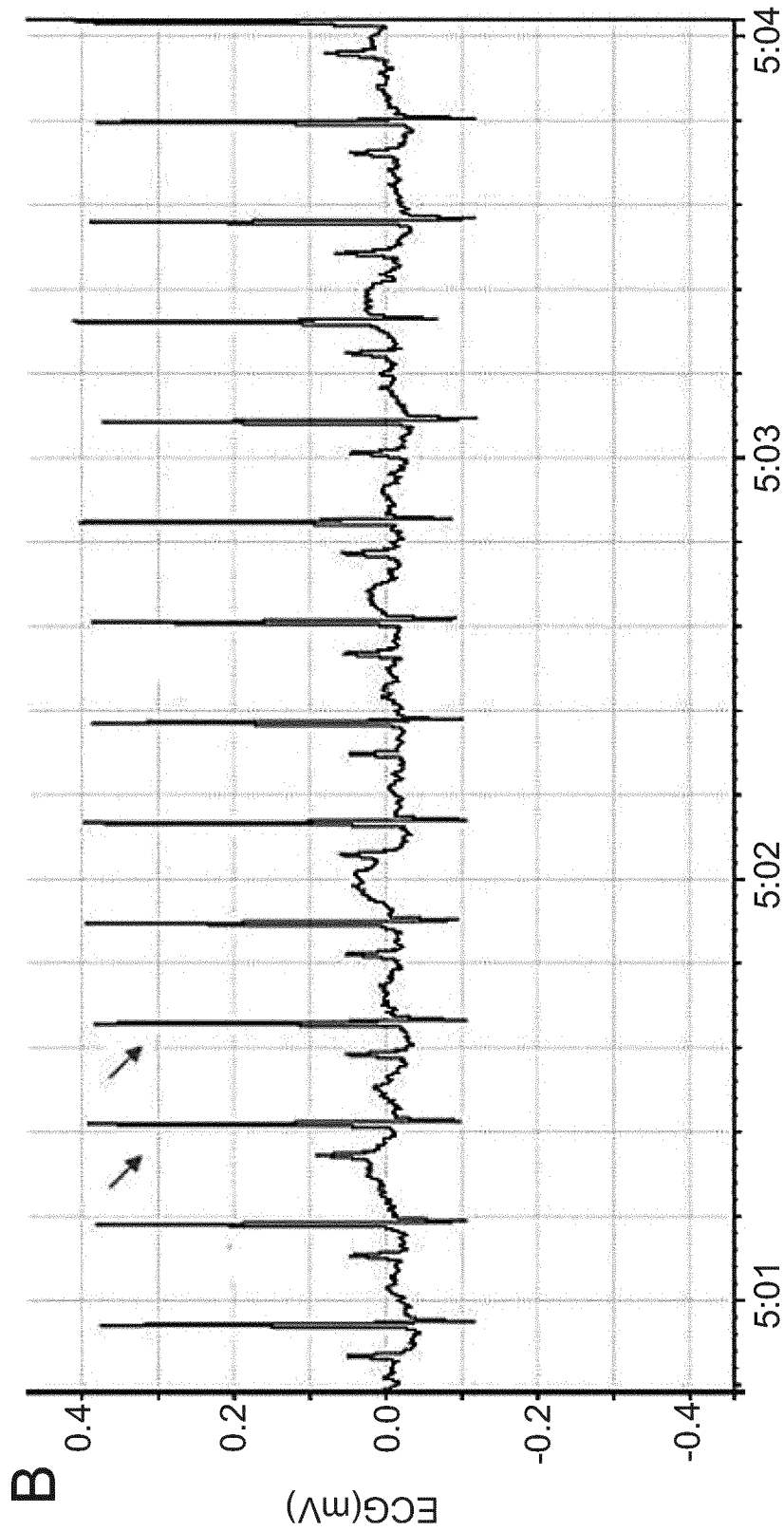
Fig. 12, ctd.

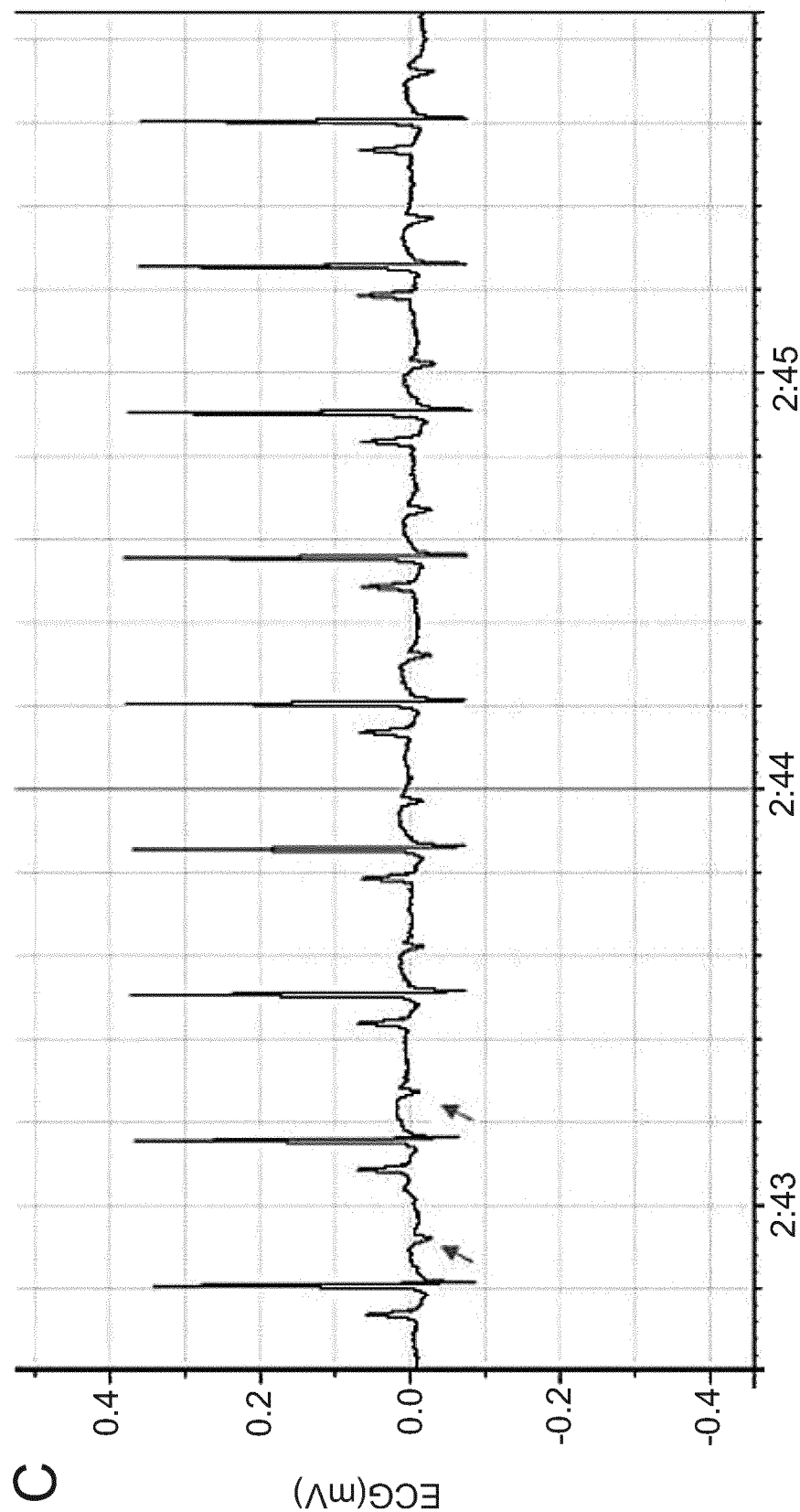
Fig. 12, ctd.

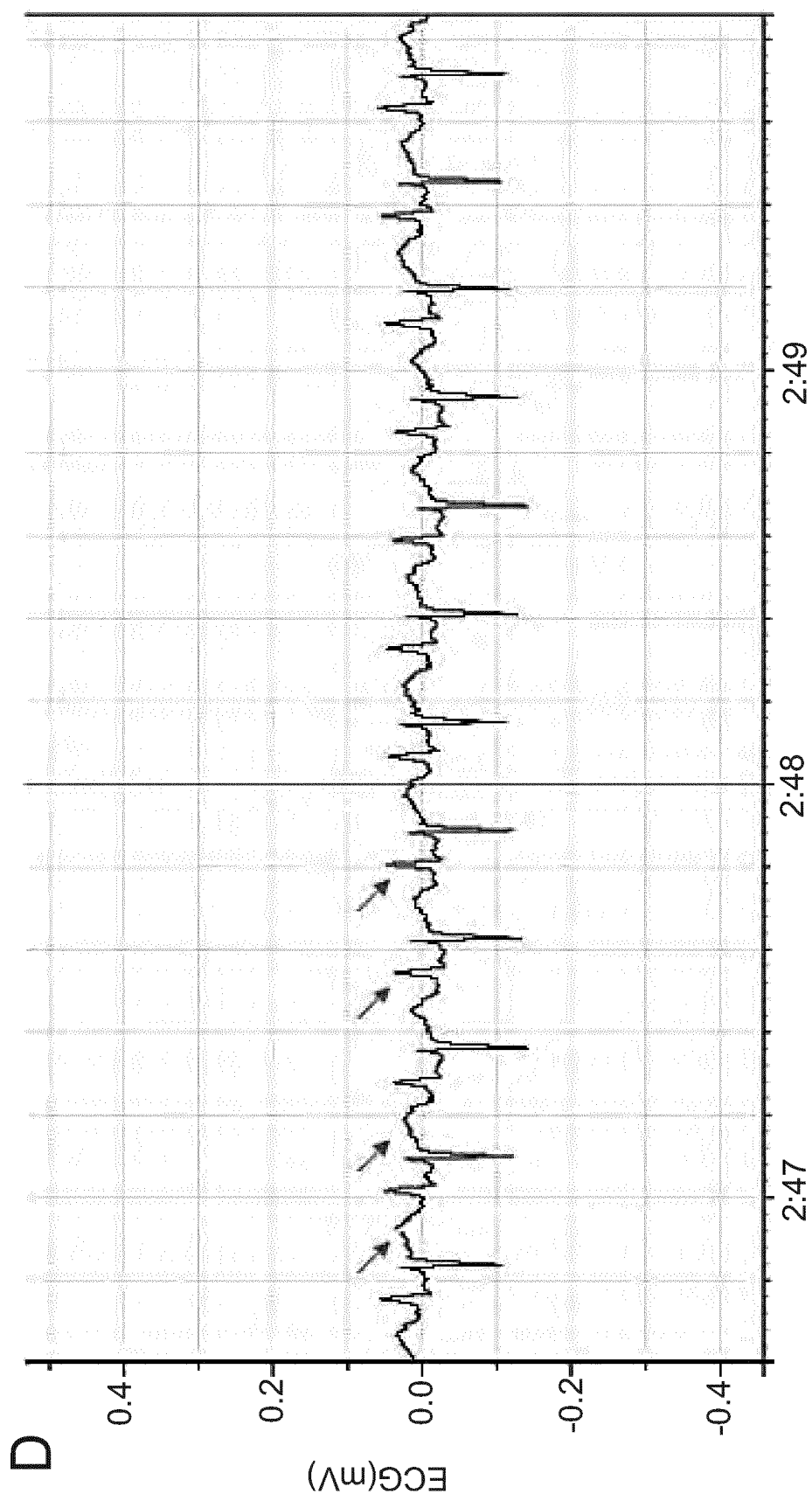
Fig. 12, ctd.

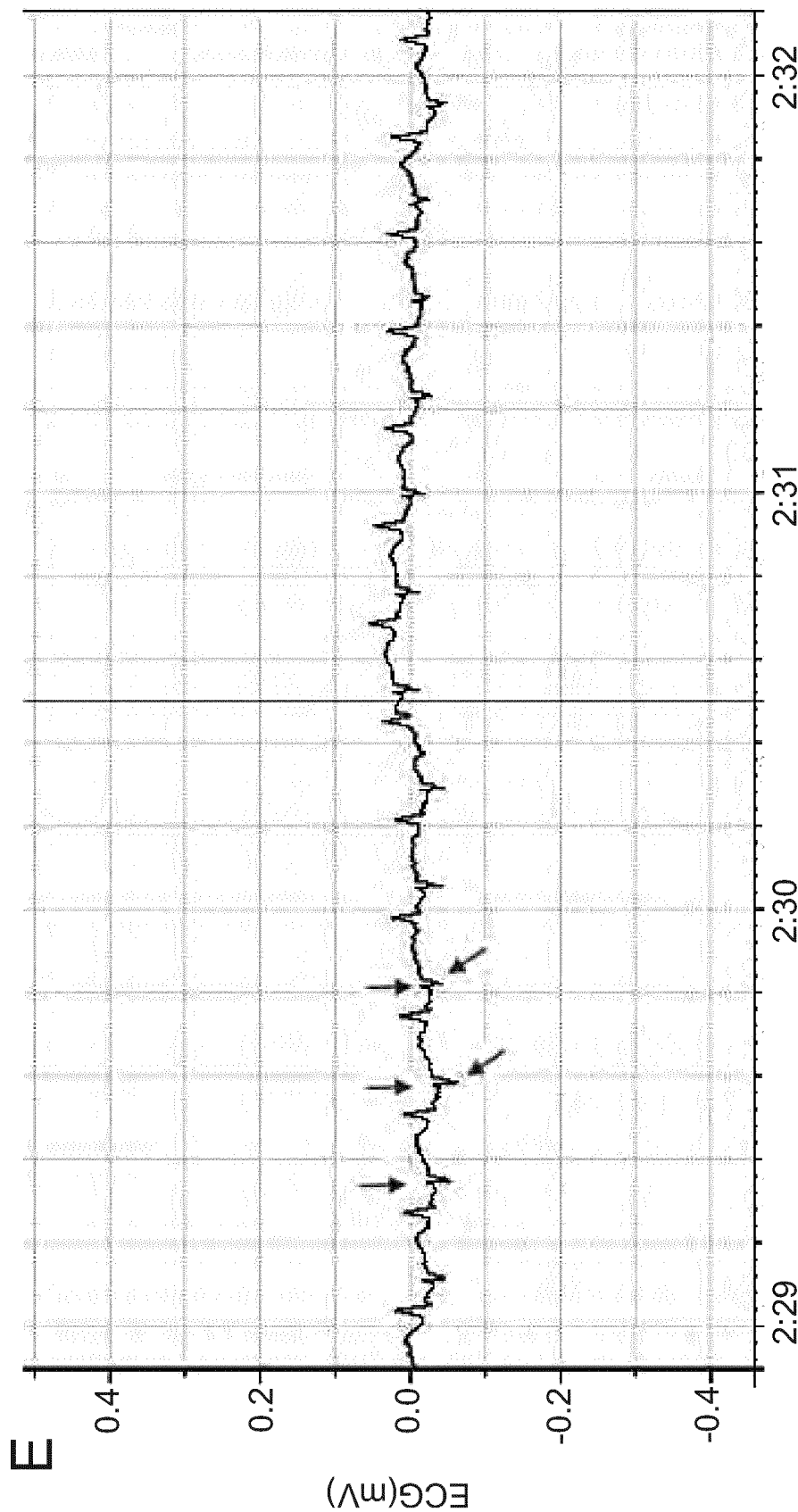
Fig. 12, ctd.

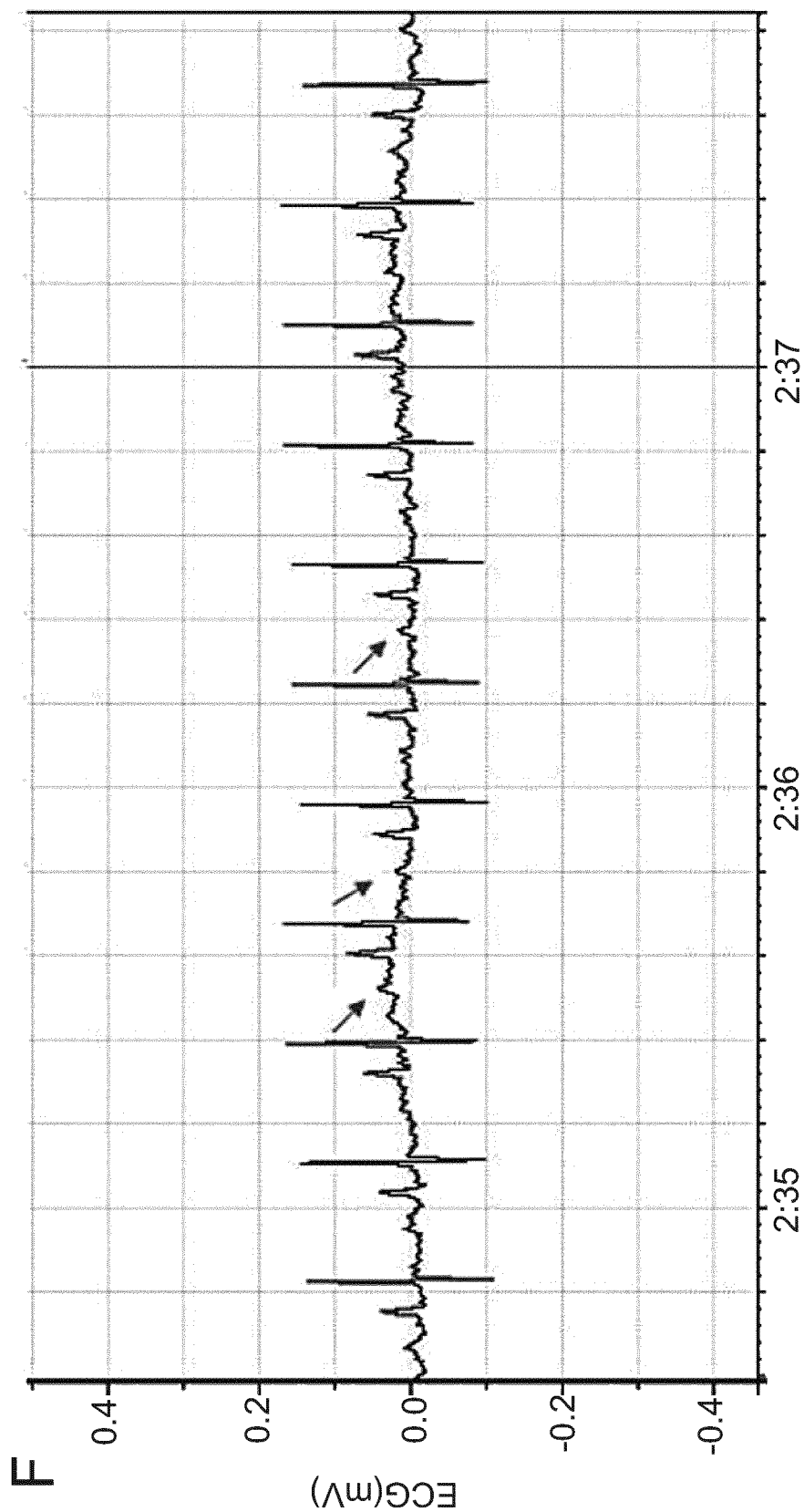
Fig. 12, ctd.

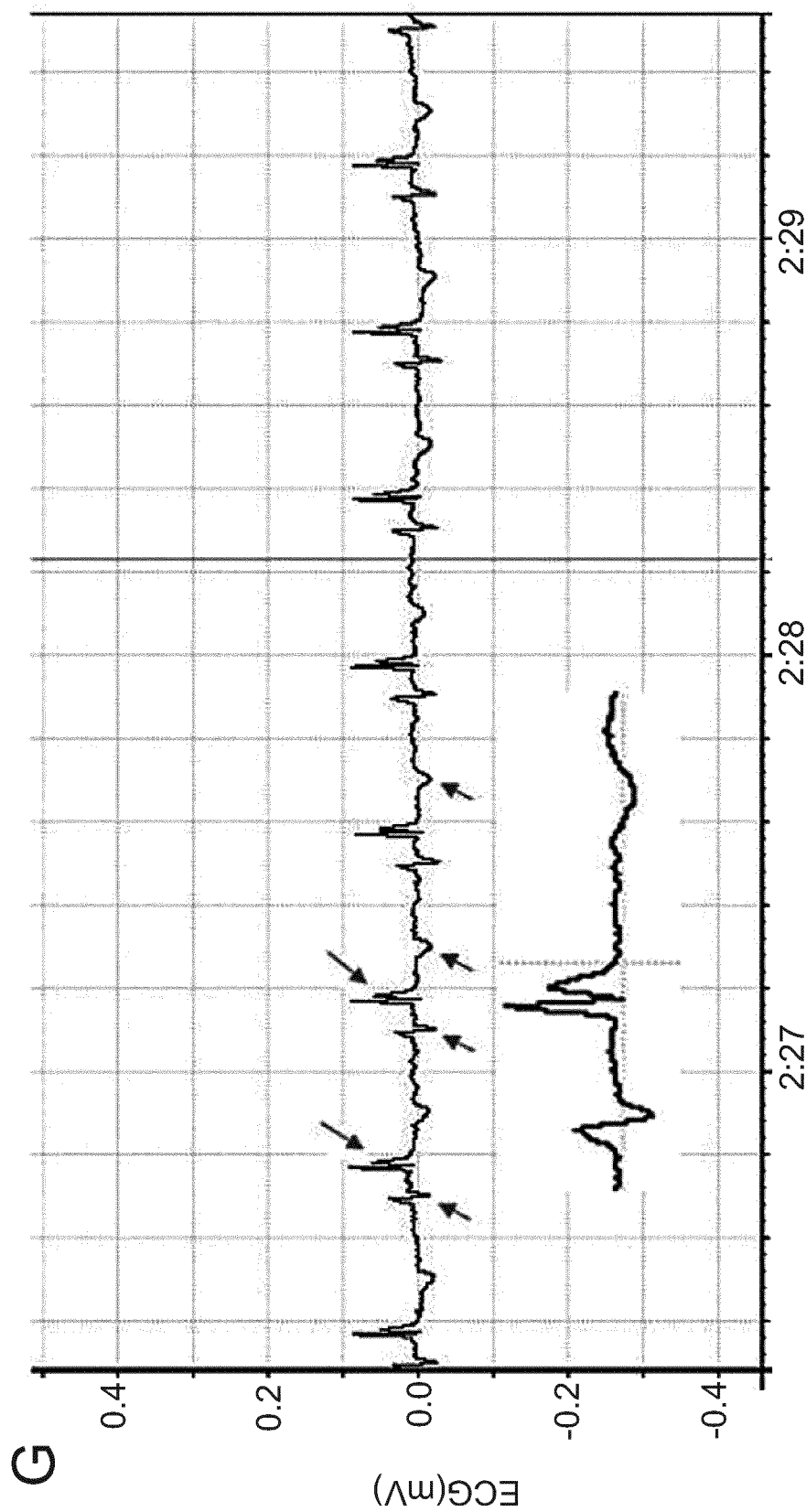
Fig. 12, ctd.

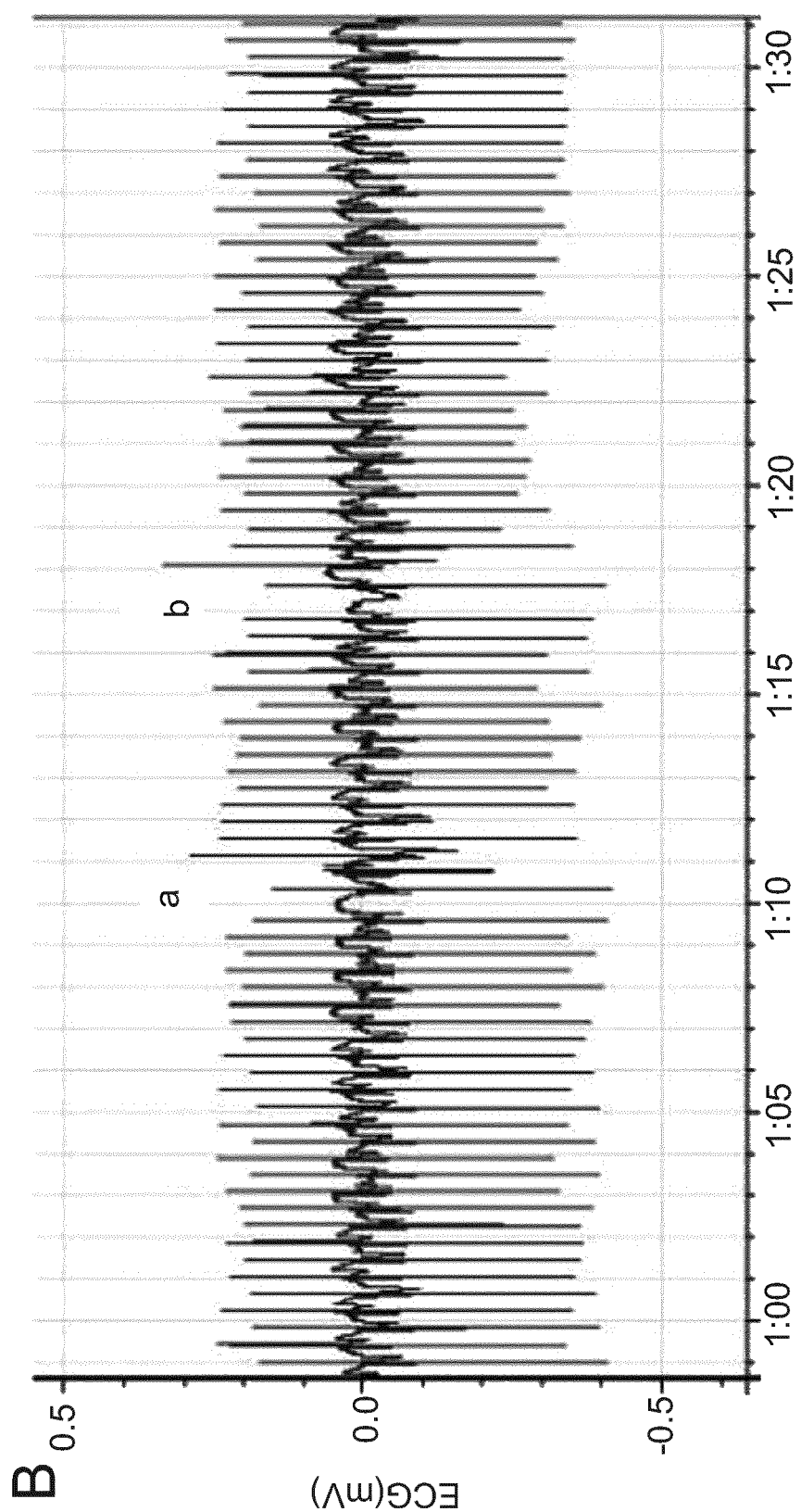
Fig. 13, ctd.

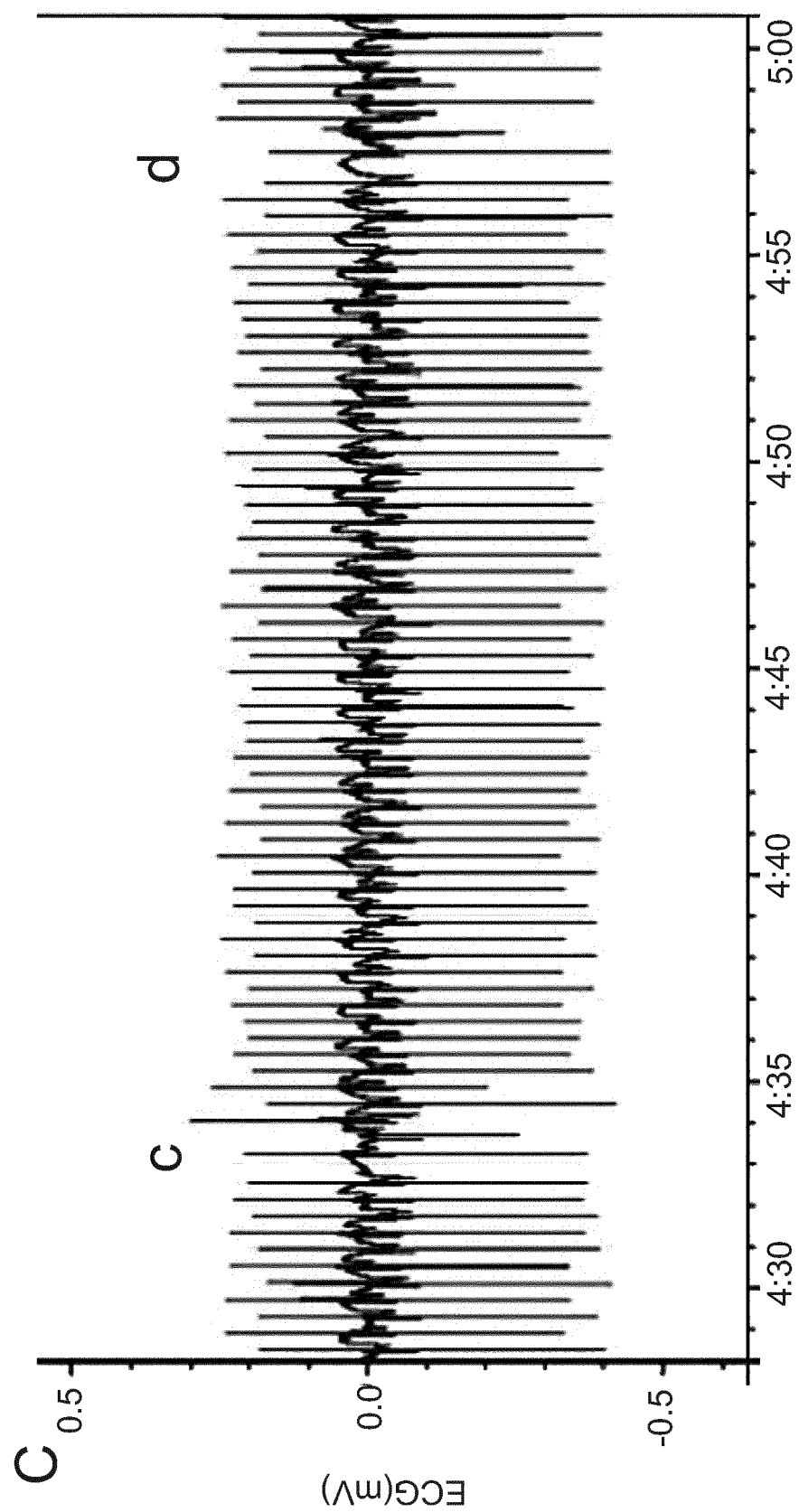
Fig. 13, ctd.

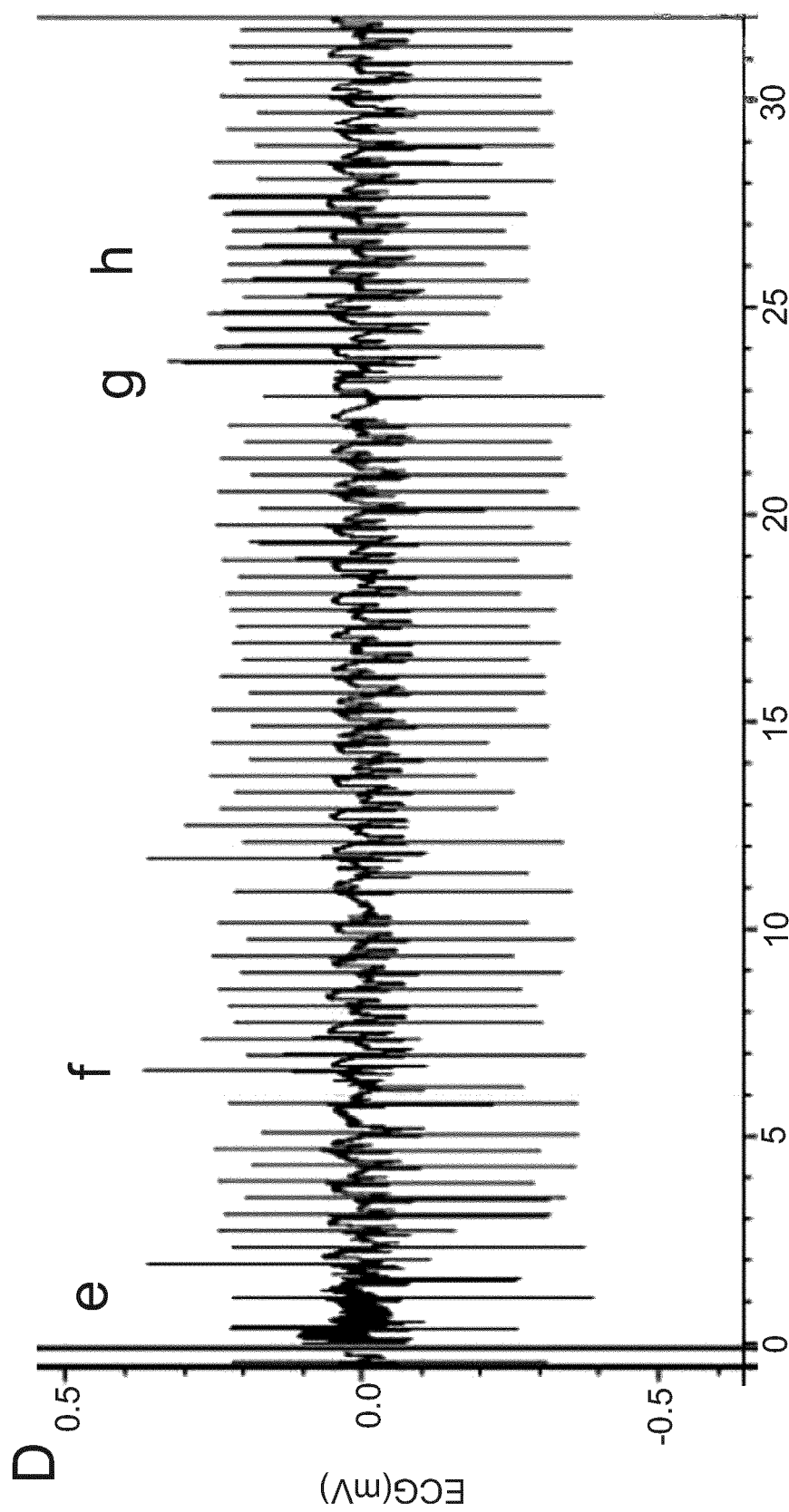
Fig. 13, ctd.

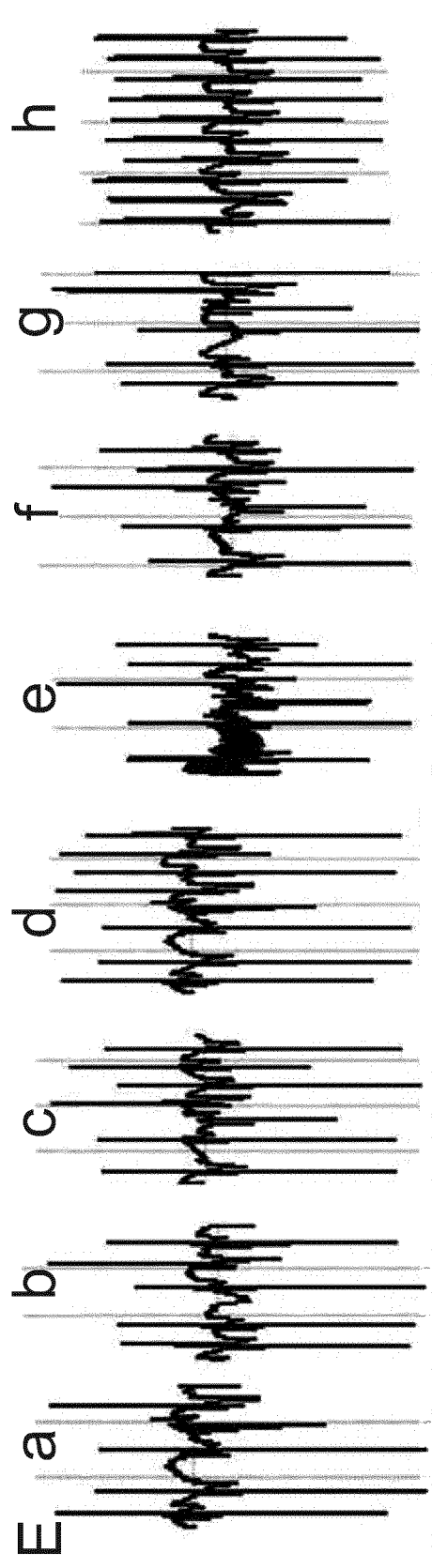
Fig. 13, ctd.

METHOD OF PREVENTING OBESITY AND CARDIOVASCULAR PROBLEMS IN POULTRY

This application is the U.S. national phase of International Application No. PCT/EP2016/050751 filed 15 Jan. 2016, which designated the U.S. and claims the benefit of U.S. Provisional Application No. 62/103,769 filed 15 Jan. 2015, and claims priority to EP Patent Application No. 15166937.1 filed 8 May 2015, the entire contents of each of which are hereby incorporated by reference.

BRIEF DESCRIPTION OF THE INVENTION

This invention relates to a method of protecting poultry which eat ad libidum from becoming obese by providing the birds with a diet comprising the combination of 25-hydroxyvitamin D ("25-OH D3" and/or "25-OH D2") and antioxidants/anti-inflammatories (ascorbic acid, Vitamin E and canthaxanthin). This combination of nutritional supplements protects poultry against various adverse effects associated with hyperphagia and related obesity, including cardio-vascular diseases. It also relates to feed and feed premixes containing the combination of 25-hydroxyvitamin D and the antioxidants/anti-inflammatories used for this purpose.

BACKGROUND OF THE INVENTION

Poultry can exhibit hyperphagia, i.e. they do not self-regulate their eating and are at risk of becoming obese. Obese poultry can suffer from many adverse conditions, including ovarian and cardiovascular related diseases, and thus it is desirable to prevent or at least minimize the occurrence of obesity in the flock. Under production conditions, this is often done by restricting the amount of feed available to the flock. However, individuals may become aggressive and fight other flock members for food, thus becoming obese and inflicting injury on other birds.

In contrast to feed-restricted hens, voluntary feeding also induced metabolic dysregulations that comprised enhanced adiposity; hepatic triacylglycerol accumulation; and elevated concentrations of plasma glucose, non-esterified fatty acids, very low density lipoprotein, triacylglycerol, phospholipids, ceramide and sphingomyelin. Furthermore, hepatic and circulating ceramide and sphingomyelin accumulation, and up-regulation of proinflammatory IL-1β expression in liver and adipose tissues systemically manifested the development of lipotoxicity in feed-satiated hens. Ceramide is a key intermediate linking certain nutrients (i.e. saturated fats) and inflammatory cytokines (e.g. tumor necrosis factor-α, TNFα) to the regulation of cell function and antagonizing insulin signaling and mitochondrial function. Moreover, as a result of its toxic effects on particularly susceptible cell types, ceramide has the capacity to damage the heart, pancreas, and vasculature. Lipotoxicity leading to impaired ovarian dysfunctions, including follicle atresia, ovarian regression, and a decline of circulating estradiol levels in feed-satiated hens, was further exemplified by ceramide accumulation and up-regulation of IL-1β, serine palmitoyltransferase, and sphingomyelinase transcript abundance, but suppressed protein kinase Akt activation within the hierarchical follicles. In vivo evidence has thus delineated the actions of ceramide and IL-1β in mediating overfeeding-induced follicle atresia and progression of ovarian involution in broiler hens.

Despite restricted feeding regimen strictly implemented in commercial broiler breeder flocks, it is still very easy to overfeed breeder hens due to their intrinsic hyperphagia. Furthermore, breeder farm managers are confronted as to when and how to feed before and during the start of egg production as well as towards, during and after peak production. The basic fundamental question to ask what and how management and nutritional tools breeder farm managers can apply and implement to ameliorate the adverse and deleterious effects of reproductive efficiency associated with obesity in overweight hens.

Hy•D® (registered trademark for 25-OH-D3; available from DSM Nutritional Products, Switzerland) has been used to promote bone health in poultry.

The combination of 25-OH D3 and canthaxanthin has also been used in poultry. WO2010/057811 (DSM IP ASSETS, BV) describes this combination for use in improving hatchability, fertility, and lower embryo mortality in poultry. The combination is commercially available under the registered trademark MAXICHICK. There is no mention in the patent publication of the inclusion of ascorbic acid, nor the uses to ameliorate the adverse effects of hyperphagia-related obesity.

Vitamin C (ascorbic acid) is often not included as a supplement in poultry diets, as chickens under normal rearing conditions, can produce sufficient Vitamin C. However, it has been used in some specific conditions, such as in heat stress situations.

Vitamin E is generally added to poultry feed. Recommended doses for broilers tends to range from about 50-100 IU/kg feed, depending on the age of the animal.

WO14/191153 (DSM IP ASSETS B.V) teaches the combination of canthaxanthin and at least one of Vitamin C, Vitamin E, selenium, and optionally at least one of thymol, eugenol, vanillin and gamma-terpinene can improve immune statues, bone health, skeletal development and growth and feed conversion, particularly when flocks are subject to stress associated with vaccination.

WO14/202433 (DSM IP ASSETS B.V) teaches the combination of canthaxanthin and 25-OH D3 to improve internal egg quality, i.e. retaining the freshness of an egg by preventing the egg white from becoming watery and spreading out when broken onto a flat surface, and retaining the egg's Naught unit value (height of the albumin). There is no teaching to add ascorbic acid to the combination, nor for its use in ameliorating the adverse effects of hyperphagia-related obesity.

There is a need to modulate weight gain in poultry fed an ad-libitum diet.

DETAILED DESCRIPTION OF THE INVENTION

It has been found, in accordance with this invention, that the combination of 25-hydroxy vitamin D (25-OH D3 and/or 25-OH D2) and antioxidants/anti-inflammatories modulates weight gain. Poultry fed ad libitum a diet containing the combination of this invention gain an appropriate amount of weight and do not become obese or experience other detrimental effects associated with hyperphagia-related obesity, including cardiovascular problems.

As 25-OH D2 and 25-OH D3 may act in a similar fashion after administration, it is envisioned that either may be used separately in combination with antioxidants/anti-inflammatories or a mixture of both 25-OH D3 and 25-OH D2 may be used in combination with antioxidants/anti-inflammatories. If used together, the ratio of 25-OH D3: 25-OH D2 is not a critical part of the invention. 25-OH D3 used alone is preferred.

The antioxidants/anti-inflammatories of this invention comprise the combination of ascorbic acid, vitamin E and canthaxanthin. Thus one aspect of this invention is the combination of 25-OH D3, canthaxanthin, vitamin E and ascorbic acid for the use of modulating weight gain in poultry. Another embodiment is the combination of 25-OHD2, canthaxanthin, Vitamin E and ascorbic acid for the use of modulating weight gain in poultry. Another embodiment is the combination of 25-OHD3, 25-OHD2, canthaxanthin, Vitamin E and ascorbic acid for the use of modulating weight gain in poultry.

It has also been found in accordance with this invention that the combination of 25-OH D and antioxidants/anti-inflammatories can also improve cardiovascular health in poultry. Thus another aspect of this invention is the use of the combination to improve cardiovascular health, and/or ameliorate cardiovascular problems, particularly in poultry fed ad libitum. Further, another aspect of this invention is a method of improving cardiovascular health in a poultry flock comprising administering a combination of 25-OH D and antioxidants/anti-inflammatories to the flock, said combination being administered in addition to a basal diet.

Another aspect of this invention is the combination of 25-OH D, canthaxanthin, vitamin E and ascorbic acid, which optionally further comprises at least one further bio-active ingredient selected from the group consisting of: Vitamin D, Vitamin B2, Vitamin B6, Niacin, Zinc, Copper, Manganese, and Selenium for the use of modulating weight gain and/or ameliorating cardiovascular problems in poultry. Preferably the 25-OH D is 25-OH D3. Preferably at least Vitamin D is a further bio-active ingredient. Sometimes the further bio-active ingredients include at least Vitamin D and Selenium. In some cases, all the further bio-active ingredients are added.

A further aspect is the combination of 25-OH D, canthaxanthin, vitamin E and ascorbic acid which optionally further comprises at least one further bio-active ingredient selected from the group consisting of Vitamin D, Vitamin B2, Vitamin B6, Niacin, Pantothenic Acid, Folic Acid, Biotin, Zinc, Copper, Manganese, Selenium, and combinations thereof for the use of modulating weight gain and/or ameliorating cardiovascular problems in poultry. Preferably the 25-OH D is 25-OH D3. Sometimes, the further bio-active ingredient includes biotin. Sometimes the further bio-active ingredient includes Vitamin D and biotin. Sometimes the further bio-active ingredient includes all the aforementioned optionally bio-active ingredients.

Another aspect of this invention is a poultry feed comprising the combination of 25-OH D2 or 25-OH D3 or mixtures thereof, ascorbic acid, Vitamin E and canthaxanthin for the use of modulating weight gain and/or ameliorating cardiovascular problems in poultry.

Yet another embodiment is poultry feed comprising the combination of 25-OH D, canthaxanthin, vitamin E and ascorbic acid, which optionally further comprises at least one further bio-active ingredient selected from the group consisting of: Vitamin D, Vitamin B2, Vitamin B6, Niacin, Zinc, Copper, Manganese, Selenium and combinations thereof for the use of modulating weight gain and/or ameliorating cardiovascular problems in poultry. Preferably the 25-OH D is 25-OH D3. Sometimes the further bio-active ingredients include at least Vitamin D and Selenium. In some cases, all the further bio-active ingredients are added.

Another embodiment is poultry feed comprising the combination of 25-OH D, canthaxanthin, vitamin E and ascorbic acid, which optionally further comprises at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium and combinations thereof for the use of modulating weight gain and/or ameliorating cardiovascular problems in poultry. Sometimes, the further bio-active ingredient includes biotin. Preferably the 25-OH D is 25-OH D3. Sometimes the further bio-active ingredient includes Vitamin D and biotin. Sometimes the further bio-active ingredient includes all the aforementioned optionally bio-active ingredients.

Yet another embodiment is poultry feed comprising the combination of 25-OH D, canthaxanthin, vitamin E and ascorbic acid, which optionally further comprises at least one further bio-active ingredient selected from the group consisting of: Vitamin D, Vitamin B2, Vitamin B6, Niacin, Zinc, Copper, Manganese, Selenium and combinations thereof for the use of providing cardiovascular protective benefits. Preferably the 25-OH D is 25-OH D3. Sometimes the further bio-active ingredients include at least Vitamin D and Selenium. In some cases, all the further bio-active ingredients are added.

Another embodiment is poultry feed comprising the combination of 25-OH D, canthaxanthin, vitamin E and ascorbic acid, which optionally further comprises at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium and combinations thereof for the use of improving cardiovascular health. Sometimes, the further bio-active ingredient includes biotin. Preferably the 25-OH D is 25-OH D3. Sometimes the further bio-active ingredient includes Vitamin D and biotin. Sometimes the further bio-active ingredient includes all the aforementioned optionally bio-active ingredients.

When using the poultry feed of this invention, the animals may be fed ad libitum and the ill effects attributable to hyperphagia normally experienced will be experienced to a lesser degree or not at all. This results in easier flock management, and eliminates the problems encountered where the flock is fed a restricted diet, but certain individual birds still exhibit hyperphagia, and may show aggressive behaviors towards other birds. Thus another aspect of this invention is a method of modulating weight gain in poultry and or improving the cardiovascular health of a flock comprising feeding the poultry a diet comprising the aforementioned feed or combination.

BRIEF DESCRIPTION OF THE FIGURES

FIGS. 16 and 17 are photos showing the effect of dietary supplementation of 25-OH-D3+antioxidants/anti-inflammatories on cardiac cell apoptosis of broiler hens with restricted or ad libitum feed intake. (at age of 35 weeks)

Figure 1:
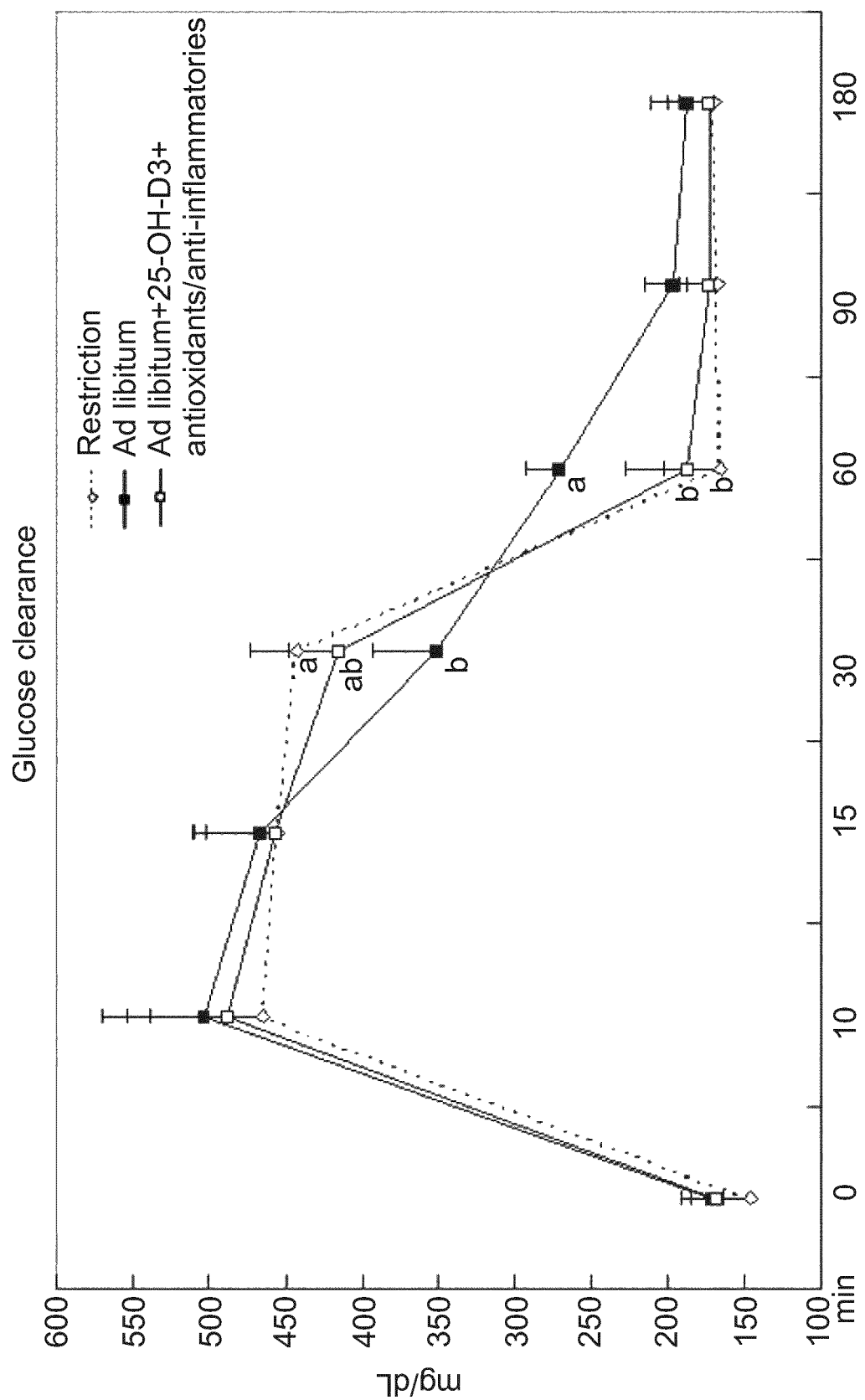
FIG. 1 shows glucose clearance and insulin secretion of broiler breeder hens in response to ad libitum feed intake in combination with 25-OH D3+antioxidants/anti-inflammatories. Hens were injected with a single dose of glucose (0.5 g/kg BW) through wing vein after 3 weeks of feeding. Blood samples were collected through cannulation of wing vein at indicated time points after glucose infusion, n=3.

As used throughout this specification and claims, the following definitions apply: "25-OH D" refers to any form of 25-hydroxyvitamin D (i.e. either 25-OH D2 or 25-OH D3, or mixes thereof). 25-OH D3 specifically refers to 25-hydroxyvitamin D3; 25-OH D2 specifically refers to 25-hydroxyvitamin D2.

"Vitamin D" means either Vitamin D2, Vitamin D3 or a combination. Vitamin D3 is preferred.

"Poultry" means any domesticated fowl, including meat-producing, table egg-producing and fertile egg-producing chickens, ducks, geese, turkeys, quail, and ostriches.

"Hyperphagia" is excessive eating; the animal does not voluntarily limit its feeding.

"Ameliorating weight gain" means that there is a lower amount of weight gained by the poultry when feeding ad libitum with ingesting the combination of 25-OH D3 and antioxidants/anti-inflammatories described herein compared to those eating the same diet without the 25-OH D3 and anti-oxidants/anti-inflammatories. The birds ingesting the combination may gain more than those fed a restricted diet.

"Ascorbic Acid" and "Vitamin C" are used interchangeably throughout the specification and claims.

"Basal diet" means that the feed used supplies the poultry with sufficient vitamins and minerals so that the poultry are vitamin and mineral replete.

"25-OH-D3+antioxidants/anti-inflammatories" means the combination of 25-OH D3, vitamin E, canthaxanthin and ascorbic acid, administered in feed as an addition to a basal diet, at a dosage range as set forth in the specification. Optionally, and preferably, additional bio-active ingredients, selected from the group consisting of: Vitamin D, Vitamin B2, Vitamin B6, Niacin, Pantothenic Acid, Folic Acid, Biotin, Zinc, Copper, Manganese, Selenium and combinations thereof are added to the 25-OHD3, vitamin E, canthaxanthin and ascorbic acid combination.

"Sudden Death" means that the individual bird died without showing previous signs or illness or trauma. Birds appear healthy, but die rapidly with a short period of wing beating and leg movement, during which they frequently flip onto their backs. They also may be found dead on their sides or breasts. There are no specific gross lesions. Recent studies indicate that dead birds have lesions in cardiomyocytes and subendocardial Purkinje cells, and this may help in diagnosis.

In one aspect of this invention the combination of 25-OH D3 and the antioxidants/anti-inflammatories are given to poultry which are vitamin replete rather than vitamin deficient. The vitamin replete status is preferably due to the use of a basal feed which supplies at least the minimum amount of vitamins and minerals for the poultry. The combination of this invention is thus preferably used in addition to the basal diet.

Metabolic Problems Reduced

Metabolic problems associated with hyperphagia and which can be lessened, reduced or eliminated through use of the feed/premix of this invention include:

a) clearance of non-esterified fatty acids
b) amelioration of plasma dyslipidemia (triglycerides, sphingomyelin, and ceramide)
c) amelioration of triglyceride and ceraminde accumulation in the liver, leg, breast muscle, and heart
d) suppression the tissue pro-inflammatory IL-1β production and plasma IL-6 concentration
e) cardiac protection and enhanced cardiac function through the up-regulation of the phosphorylation of STAT-3 (signal transducer and activator of transcription 3) in the heart.
f) suppression of the infiltration of immune cells into the heart
g) decreasing the incidence of ascites.

These above-mentioned observed improved conditions result in a lowering of mortality rate, improved insulin signaling, reduced lipotoxic development and systemic inflammation, and activation of cardio-protective mechanisms against fuel-overload induced cardiac pathogenesis.

2. Cardio-Vascular Problems, Including Sudden Death

Birds in a flock can experience a sudden death, i.e. the cause of death is not readily apparent. This was investigated this further, as is detailed in EXAMPLE 4, and the results are herein summarized. We investigated this phenomenon in flocks fed ad libitum and a restricted diet, with or without the combination of 25-OH D3 and antioxidants/anti-inflammatories. Some of our results are set forth below.

It has been found, in accordance with this invention, that the combination of 25-OH D3 and the antioxidants/anti-inflammatories, that in In birds fed ad libitum, sudden death birds (i.e, birds which have undergone sudden death) which had been fed with25-OH-D3+antioxidants/anti-inflammatories had higher body weight, but lower relative liver, abdominal fat, and heart weight.

In the birds with sudden death, ad libitum feeding caused cardiac adaptive hypertrophy; and some of the hypertrophic growth may develop pathologically into ventricle dilation. As a result, the heart requires a higher contractility to maintain pumping function to meet the need of blood supply for oxygen delivery to the peripheral tissues. This condition may have caused heart failure.

Importantly, we found that 25-OH-D3+antioxidants/anti-inflammatories decreased cardiac pathogenic progression and thereby the incidence of heart failure in birds fed ad libitum. Thus another aspect of this invention is the use of 25-OH-D3+antioxidants/anti-inflammatories to reduce the amount of cardiac problems leading to sudden death in poultry, particularly those which are fed ad libidum.

In both restricted and ad libitum fed birds, birds with 25-OH-D3+antioxidants/anti-inflammatories exhibited less adaptive hypertrophic growth, supporting the hypothesis that most excessive fuels may be partitioned to the muscle, and thereby, hypertrophic growth of the heart for increased pumping function cannot meet the need of oxygen supply for higher growth rate (muscle) and thus may provoke cardiac arrhythmia and failure.

25-OH-D3+antioxidants/anti-inflammatories were seen to have the following effects:
Decreased the incidence of cardiac morbidities (dilation, pericardial effusion, rupture) observed in necropsies of in the dead birds;
Decreased the amount of irregular incidence of ECG patterns;
Decreased arrhythmia of broiler hens fed ad libitum;
ameliorated sudden death induced by cardiac morbidities;
ameliorated cardiac fibrosis in hens fed ad libitum;
ameliorated chronic systemic inflammation in hens fed ad libitum.
ameliorated cardiac cell apoptosis in hens with restricted or ad libitum feed intake.

Thus, the 250H D3+antioxidants can protect the cardiovascular system. Thus another aspect of this invention is the use of 25-OH D3+antioxidants-anti-inflammatories to protect the cardiovascular system, wherein the protection comprises at least one effect selected from the group consisting of: decreasing the incidence of cardiac morbidities (dilation, pericardial effusion, rupture); decreasing the amount of irregular incidence of ECG patterns; decreasing arrhythmia; ameliorated the number of sudden death induced by cardiac morbidities in a flock; ameliorating cardiac fibrosis; ameliorating chronic systemic inflammation; and ameliorating cardiac cell apoptosis.

Dosages

In one aspect of this invention the combination of 25-OH D3 and the antioxidants/anti-inflammatories are given to poultry which are vitamin replete rather than vitamin deficient. The vitamin replete status is preferably due to the use of a basal feed which supplies at least the minimum amount of vitamins and minerals for the poultry. The combination of this invention is thus preferably used in addition to the basal diet.

25-OH D3:
The amount of 25-OH D3 can range from 15-200 µg/kg feed. Preferably, the amount of 25-OH D3 is from 35-150 µg/kg feed. For feed with a low dose of the combination of the invention, 35 µg per kg 25-OH D3/feed is preferred; for food with a medium dose of the combination, 69 µg per kg feed is preferred; and for food with a high dose of 150 µg feed is preferred.

Vitamin E:
The amount of Vitamin E can range from 40-400 mg/kg feed. Preferably the amount is 80-300 mg/kg feed. For feed with a low dose of the combination of the invention, 80 mg/kg Vitamin E is preferred. For feed with a medium dose, 150 mg Vitamin E is preferred; for feed with a high dose, 300 mg/kg Vitamin E is preferred.

Canthaxanthin:
The amount of canthaxanthin can range from 1-15 mg/kg feed. Preferably the amount is 3-12 mg/kg feed. For feed with a low dose of the combination of the invention, 3 mg/kg canthaxanthin is preferred. For feed with a medium dose, 6 mg canthaxanthin is preferred; for feed with a high dose, 12 mg/kg canthaxanthin is preferred.

Ascorbic Acid:
The amount of ascorbic acid can range from 40-400 mg/kg feed. Preferably the amount is 100-300 mg feed. For feed with a low dose of the combination of the invention, 100 mg/kg ascorbic acid is preferred. For feed with a medium dose, 150 mg ascorbic acid is preferred; for feed with a high dose, 300 mg/kg ascorbic acid is preferred.

Thus specific preferred feeds of this invention comprise the following dosages (all amounts are per kg/feed):

Preferred Feed #1:
25-OH D3: 15-200 µg,
Vitamin E: 40-400 mg,
Canthaxanthin: 1-15 mg; and
Ascorbic acid: 40-400 mg.

Preferred Feed #2:
25-OH D3: 35-150 µg,
Vitamin E: 80-300 mg,
Canthaxanthin: 3-12 mg, and
Ascorbic acid: 80-300 mg Preferred Feed #3: (Low dose feed) This feed is preferred for mildly obese poultry.
25-OH D3: 35 µg
Vitamin E: 80 mg
Canthaxanthin: 3 mg
Ascorbic acid: 80 mg.

Preferred Feed #4 (medium dose feed) This feed is preferred for moderately to severely obese poultry:
25-OH D3: 69 µg
Vitamin E: 150 mg
Canthaxanthin: 6 mg
Ascorbic acid: 150 mg.

Preferred Feed #5 (high dose feed) This feed is preferred for severely obese poultry:
25-OH D3: 150 µg
Vitamin E: 300 mg
Canthaxanthin: 12 mg
Ascorbic acid: 300 mg.

The ratios of the above antioxidants/anti-inflammatories relative to each other may range as follows:
Vitamin E to Vitamin C may range from 1-10:10-1; preferably 1-5:5-1; and more preferably 1.5:1 to 1:1.5, and most preferably 1:1.

Vitamin E or Vitamin C to Canthaxanthin may range from 40:1 to 1:1; preferably from 20:1 to 1:1; and more preferably from 10:1 to 1:1

Preferred ratios include the following

| Vit E | Vit C | Canthaxanthin |
|---|---|---|
| 40 | 40 | 1 |
| 20 | 20 | 1 |
| 10 | 10 | 1 |

Optional Additional Ingredients

To each of the feeds listed above, at least one of the additional ingredients may be added. Preferably at least one, and more preferably more than one of the following ingredients are added. In other embodiments, all the following ingredients are added:

Vitamin D3—generally this is present in poultry diets at approximately 2500 IU per kg feed. In accordance with this invention, if desired, the amount of Vitamin D is increased to at least 3000 IU per kg.

Vitamin B2: this can be added at 3-25 mg per kg; preferably from 6-20 mg/kg. For low dose feed, 6 mg/kg is preferred. For medium dose feed, 14 mg/kg is preferred; and for high dose feed 20 mg/kg is preferred.

Niacin: this can be added at 25-300 mg per kg feed. Preferably it ranges from 60-200 mg/kg. For low dose feed, 60 mg/kg is preferred. For medium dose feed, 120 mg/kg is preferred; and for high dose feed 200 mg/kg is preferred.

Pantothenic acid: this can be added at 10-120 mg per kg feed. Preferably it ranges from 15-80 mg/kg. For low dose feed, 15 mg/kg is preferred. For medium dose feed, 30 mg/kg is preferred; and for high dose feed 80 mg/kg is preferred.

Folic acid: this can be added at 1-8 mg per kg feed. Preferably it ranges from 2-6 mg/kg. For low dose feed, 2 mg/kg is preferred. For medium dose feed, 4 mg/kg is preferred; and for high dose feed 6 mg/kg is preferred.

Biotin: this can be added at 0.05-1.0 mg/kg feed. Preferably it ranges from 0.2-0.8 mg/kg. For low dose feed, 0.2 mg/kg is preferred. For medium dose feed, 0.4 mg/kg is preferred; and for high dose feed 0.8 mg/kg is preferred.

Zinc: this can be added at 50-300 mg/kg feed. Preferably it ranges from 70-250 mg/kg. For low dose feed, 70 mg/kg is preferred. For medium dose feed, 125 mg/kg is preferred; and for high dose feed 250 mg/kg is preferred.

Copper: this can be added at 5-50 mg/kg feed. Preferably it ranges from 10-30 mg/kg. For low dose feed, 10 mg/kg is preferred. For medium dose feed, 20 mg/kg is preferred; and for high dose feed 30 mg/kg is preferred.

Manganese: this can be added at 50-300 mg/feed. Preferably it ranges from 80-270 mg/kg. For low dose feed, 80 mg/kg is preferred. For medium dose feed, 150 mg/kg is preferred; and for high dose feed 270 mg/kg is preferred.

Selenium: this can be added at 0.05-0.6 mg/kg feed. Preferably it ranges from 0.1-0.4 mg/kg. For low dose feed, 0.1 mg/kg is preferred. For medium dose feed, 0.3 mg/kg is preferred; and for high dose feed 0.5 mg/kg is preferred.

Premixes can be made to give the above-mentioned doses and preferred doses. One premix which forms part of this invention is formulated so that 1 gram of premix is added to one kilogram feed, and that the resulting feed contains the dosages described in any of the given dosages above. The amounts of the individual ingredients can, of course be varied so that one kilogram of premix is added to one metric ton of feed, and that the resulting feed contains the dosages described in any of the given dosages above. There are specific illustrations of this in the Examples, below.

Further, it is envisioned that the combinations specified herein may be added to any commercially available poultry food, and thus the total amount of 25-OHD3 and antioxidants/anti-inflammatories present may be equal to the amount originally present in the food plus the addition as specified herein. It is also envisioned that the 25-OHD3 and antioxidants/anti-inflammatories as specified herein are the sole additions to a basal diet which contains at least the minimum required nutrients for poultry nutrition.

The following non-limiting Examples are presented to better illustrate the invention

EXAMPLES

Example 1

Materials and Methods

A total of thirty 45-week-old broiler breeder hens (ROSS 308) were obtained from a commercial flock for the study. A basal broiler breeder laying diet was formulated as shown in Table 1. The calculated nutrient composition is shown in Table 2.

TABLE 1

Ingredient composition of the basal broiler breeder laying diets.

| Composition | %, w/w |
|---|---|
| Corn | 66.9 |
| Soybean meal | 22.2 |
| Oil fat | 1.67 |
| Ca Carbonate (ground oyster shell) | 6.36 |
| Dicalcium phosphate | 1.8 |
| Choline-Cl (70%) | 0.1 |
| Mineral Premix[1] | 0.1 |
| Copper sulfate | 0.05 |
| Vitamin Premix[2] | 0.1 |

[1]Mineral premix provided (per kg of diet for treatment groups 1, 2 and 3): Cu 18 mg; I 1.1 mg; Fe 80 mg; Mn 150 mg; Zn 125 mg; and Se 0.25 mg.
[2]Refer to Table 2 for further detail.

TABLE 2

Vitamin premix composition (provided per kg of diet)

| Vitamin | Treatments 1 and 2: 1 = restricted feeding 2 = ad libitum feeding | Treatment 3 3 = ad libitum feeding + 25-OH-D3 + antioxidants/anti-inflammatories |
|---|---|---|
| A (IU) | 10000 | 12000 |
| D3 (IU) | 2500 | 3000 |
| E (mg) | 100 | 150 |
| K3 (mg) | 3 | 5 |
| B1 (mg) | 3 | 3 |
| B2 (mg) | 8 | 14 |
| B6 (mg) | 6 | 8 |
| B12 (mg) | 0.03 | 0.03 |
| Niacin (mg) | 60 | 120 |
| Pantothenic acid (mg) | 18 | 30 |
| Folic acid (mg) | 1 | 4 |

TABLE 2-continued

Vitamin premix composition (provided per kg of diet)

| Vitamin | Treatments 1 and 2:<br>1 = restricted feeding<br>2 = ad libitum feeding | Treatment 3<br>3 = ad libitum feeding +<br>25-OH-D3 +<br>antioxidants/anti-<br>inflammatories |
|---|---|---|
| Biotin (mg) | 0.2 | 0.4 |
| C (ascorbic acid) (mg) | 0 | 150 |
| 25-OH-D3 (mcg) | 0 | 69 |
| Canthaxanthin (mg) | 0 | 6 |

TABLE 3

Calculated nutrient composition (%) of
the basal broiler breeder laying diets.

| Composition | % w/w |
|---|---|
| Crude protein | 16 |
| Crude fat | 4.2 |
| Calcium | 3.1 |
| Sodium | 0.16 |
| Total Phosphorus | 0.64 |
| Total ME | 2910 kcal/kg |

Diet was supplemented with or without 25-OH D3 at 69 mcg/kg diet in combination with antioxidants/anti-inflammatories (ascorbic acid, canthaxanthin) and enriched levels of selected vitamins. Hens were randomly allocated to 3 treatment groups according to feeding regimen (restricted and ad libitum) as follows:
1. Basal diet—restricted feeding (140 g/day)
2. Basal diet—ad libitum feeding
3. Basal diet—ad libitum feeding+25-OH-D3 at 69 mcg/kg diet+antioxidants/anti-inflammatories They were individually-housed in wire cages placed in a controlled room with 14 h:10 h light: dark period and at a temperature of 25±3° C. Water was available ad libitum. The experimental period was lasted for 10 weeks. Three weeks after the feeding trial, some birds were used for relevant plasma parameter analyses. At the end of experiment, hens were euthanized and sacrificed for tissue sample collection for further studies:
  Necropsy of Tissue Morphology
  Determination of lipid and sphingolipid profile—serum and tissues
  Determination of tissue pro-inflammatory cytokines
  Determination of insulin resistance
  Collection of tibia for bone strength analysis
  Harvesting heart (cardiomyopathy) and skeletal muscle (breast and thigh) for myopathy analyses.

Example 2

Results and Discussion

25-OH D3 and Antioxidants/Anti-Inflammatories Suppressed Adiposity and Abdominal Fat in Overfed Broiler Hens Breeder hens are capable of storing large quantities of excess energy (in the form of triglycerides) in the liver, adipose tissue and yolk of developing oocytes. Lipogenesis (i.e., the conversion of glucose to triglycerides) takes place primarily in the liver of birds and involves a series of linked, enzyme catalyzed reactions including glycolysis, the citric acid cycle and fatty acid synthesis. Hepatic lipogenesis is subject to both nutritional and hormonal control and is highly responsive to changes in the diet. Adipose tissue serves primarily as a storage site for lipid with little lipogenic activity. Differential lipogenic capacity of liver vs. adipose tissue in birds is a function of the expression of a key transcription factor, sterol regulatory element binding protein-1 (SREBP-1). The gene for SREBP-1 is highly expressed in the liver, but to a much lesser extent in adipose tissue. Moreover, the expression of a number of lipogenic enzyme genes such as fatty acid synthase, malic enzyme, acetyl CoA carboxylase, ATP citrate lyase and steroyl CoA desaturase 1 is directly influenced by SREBP-1.

Breeder hens fed ad libitum accreted more abdominal fat than those restricted fed. Dietary supplementation of 25-OHD3 and antioxidants/anti-inflammatories ameliorated the deleterious effect of ad libitum feeding on body and tissue weight, particularly on relative adipose tissue weight (adiposity) (Table 4). Tibial strength of ad libitum-fed hens was enhanced by 25-OH D3 and antioxidants/anti-inflammatories.

TABLE 4

25-OH D3 and antioxidants/anti-inflammatories on body
weight, liver weight, abdominal fat weight and tibial
strength of ad libitum-fed broiler breeder hens

|  | Restricted feeding | Ad libitum feeding | Ad libitum feeding + 25-OH-D3 + Antioxidants + anti-inflammatories | Pooled SEM[1] |
|---|---|---|---|---|
| Body weight (kg) | 3.67[c] | 4.60[a] | 4.04[b] | 0.26 |
| Liver weight (g) | 41.4[b] | 48.5[a] | 49.6[a] | 5.6 |
| Liver/body weight (%) | 1.14 | 1.06 | 1.23 | 0.18 |
| Abdominal fat weight (g) | 40.9[c] | 185.9[a] | 110.8[b] | 28.9 |
| Abdominal fat weight/body weight (%) | 1.10[c] | 4.01[a] | 2.74[b] | 0.70 |
| Tibial strength (kg/cm2) | 32.3[b] | 38.3[ab] | 44.3[a] | 3.57 |

[a-c]Within a row, means without a common superscript differ (P < 0.05).
[1]Pooled standard error of the mean.

25-OH D3 and Antioxidants/Anti-Inflammatories Lowered Mortality and Improved Egg Production, Ovarian Morphology and Plasma 17β Estradiol Level Secretion of estradiol is the hallmark of successful ovulatory follicles. In addition to its role in triggering the preovulatory surge of gonadotropins, estradiol is an important intra-ovarian growth, differentiation, and survival factor. Inclusion of 25-OH D3 and antioxidants/anti-inflammatories reduced mortality and incidence of ovarian degeneration and ovarian-tumor-like morphology, increased egg production and sustained plasma estradiol levels in birds under ad libitum feed intake.

25-OH D3 and Antioxidants/Anti-Inflammatories Ameliorated Impaired Glucose Clearance and Insulin Sensitivity Dietary inclusion of 25-OH D3 and antioxidants/anti-inflammatories improves insulin resistance as evidenced by ameliorating fasting plasma glucose and non-esterifed fatty acid level in overfed hens for 10 weeks (Table 6). In glucose clearance test, lean hens showed a very sharp clearance rate between 30-60 min after glucose infusion, and conversely obese hens had a very sluggish clearance rate between 30-90 min (FIG. 1). In insulin secretion, obese hens showed a higher plasma insulin level under fasting status and after glucose infusion when compared to lean hens (FIG. 1). Both glucose clearance and glucose-induced insulin secretion were corrected by 25-OH D3 and antioxidants/anti-inflammatories inclusion in overfed hens for 3 weeks (FIG. 1).

TABLE 5

25-OH D3 and antioxidants/anti-inflammatories on plasma glucose, non-esterified fatty acid (NEFA) and insulin of ad libitum-fed broiler breeder hens

|  | Restricted feeding | Ad libitum feeding | Ad libitum feeding + 25-OH-D3 ++ antioxidants/ anti-inflammatories | Pooled SEM[1] |
|---|---|---|---|---|
| After 3 weeks of feeding |  |  |  |  |
| Plasma glucose (mg/dL) | 181.5 | 202.5 | 188.5 | 11.9 |
| Plasma NEFA (μmole/mL) | 0.21[b] | 0.35[a] | 0.25[b] | 0.05 |
| After 10 weeks of feeding |  |  |  |  |
| Plasma glucose (mg/dL) | 180.6[b] | 212.6[a] | 195.6[b] | 12.7 |
| Plasma NEFA (μmole/mL) | 0.35[b] | 0.44[a] | 0.33[b] | 0.05 |
| Fasting plasma insulin | 1.38 | 1.15 | 1.59 | 0.21 |
| Glucose-induced insulin | 2.66[a] | 1.97[b] | 2.46[a] | 0.36 |

[a-b]Within a row, means without a common superscript differ (P < 0.05).
[1]Pooled standard error of the mean.

25-OH D3 and Antioxidants/Anti-Inflammatories Ameliorated Dyslipidemia

Ad libitum-fed hens elevated plasma triglyceride, ceramide and sphingomyelin levels. However, supplementation of combined 25-OH D3 and antioxidants/anti-inflammatories lowered the level of these lipid metabolites in the plasma of ad libitum-fed hens (Table 6).

TABLE 6

25-OH D3 and antioxidants/anti-inflammatories on plasma triacyglycerol, ceramide and sphingomyelin of ad libitum-fed broiler breeder hens

|  | Restricted feeding | Ad libitum feeding | Ad libitum feeding + 25-OH-D3 ++ antioxidants/ anti-inflammatories | Pooled SEM[1] |
|---|---|---|---|---|
| After 3 weeks of feeding |  |  |  |  |
| Plasma triacyglycerol (mg/mL) | 15.6 | 17.4 | 14.5 | 2.9 |
| Plasma ceramide (nmole/mL) | 11.5[b] | 18.2[a] | 13.5[b] | 2.83 |
| Plasma sphingomyelin (μmole/mL) | 0.14[b] | 0.28[a] | 0.16[b] | 0.05 |
| After 10 weeks of feeding |  |  |  |  |
| Plasma triacyglycerol (mg/mL) | 12.75[b] | 15.2[a] | 11.5[b] | 2.2 |

TABLE 6-continued

25-OH D3 and antioxidants/anti-inflammatories on plasma triacyglycerol, ceramide and sphingomyelin of ad libitum-fed broiler breeder hens

|  | Restricted feeding | Ad libitum feeding | Ad libitum feeding + 25-OH-D3 ++ antioxidants/ anti-inflammatories | Pooled SEM[1] |
|---|---|---|---|---|
| Plasma ceramide (nmole/mL) | 8.1[b] | 12.3[a] | 8.8[b] | 1.65 |
| Plasma sphingomyelin (μmole/mL) | 0.15[b] | 0.22[a] | 0.12[b] | 0.05 |

[a-b]Within a row, means without a common superscript differ (P < 0.05).
[1]Pooled standard error of the mean.

25-OH D3 and Antioxidants/Anti-Inflammatories Reduced Accumulation of Tissue Triglyceride and Ceramide Content Accumulation of triglyceride and ceramide in the liver, heart and leg muscles was lower in hens fed supplemental 25-OH D3 and antioxidants/anti-inflammatories than in those fed ad libitum (Table 7).

TABLE 7

25-OH D3 and antioxidants/anti-inflammatories on tissue triacyglycerol and ceramide content of ad libitum-fed broiler breeder hens

|  | Restricted feeding | Ad libitum feeding | Ad libitum feeding + 25-OH-D3 + Antioxidants + anti-inflammatories | Pooled SEM[1] |
|---|---|---|---|---|
| Triacyglycerol (mg/g tissue) |  |  |  |  |
| Liver | 69.0[b] | 94.8[a] | 79.8[a] | 10.6 |
| Heart | 33.1[b] | 55.6[a] | 45.6[a] | 6.8 |
| Breast muscle | 15.6 | 18.0 | 17.4 | 0.05 |
| Leg muscle | 30.2[c] | 52.3[a] | 41.2[b] | 6.6 |
| Ceramide (mg/g tissue) |  |  |  |  |
| Liver | 174.5[b] | 287.9[a] | 235.0[a] | 52.7 |
| Heart | 17.5[c] | 30.2[a] | 23.5[b] | 2.4 |
| Breast muscle | 2.25 | 2.91 | 2.52 | 0.54 |
| Leg muscle | 4.12[b] | 7.12[a] | 6.01[a] | 0.85 |

[a-b]Within a row, means without a common superscript differ (P < 0.05).
[1]Pooled standard error of the mean.

Figure 2:
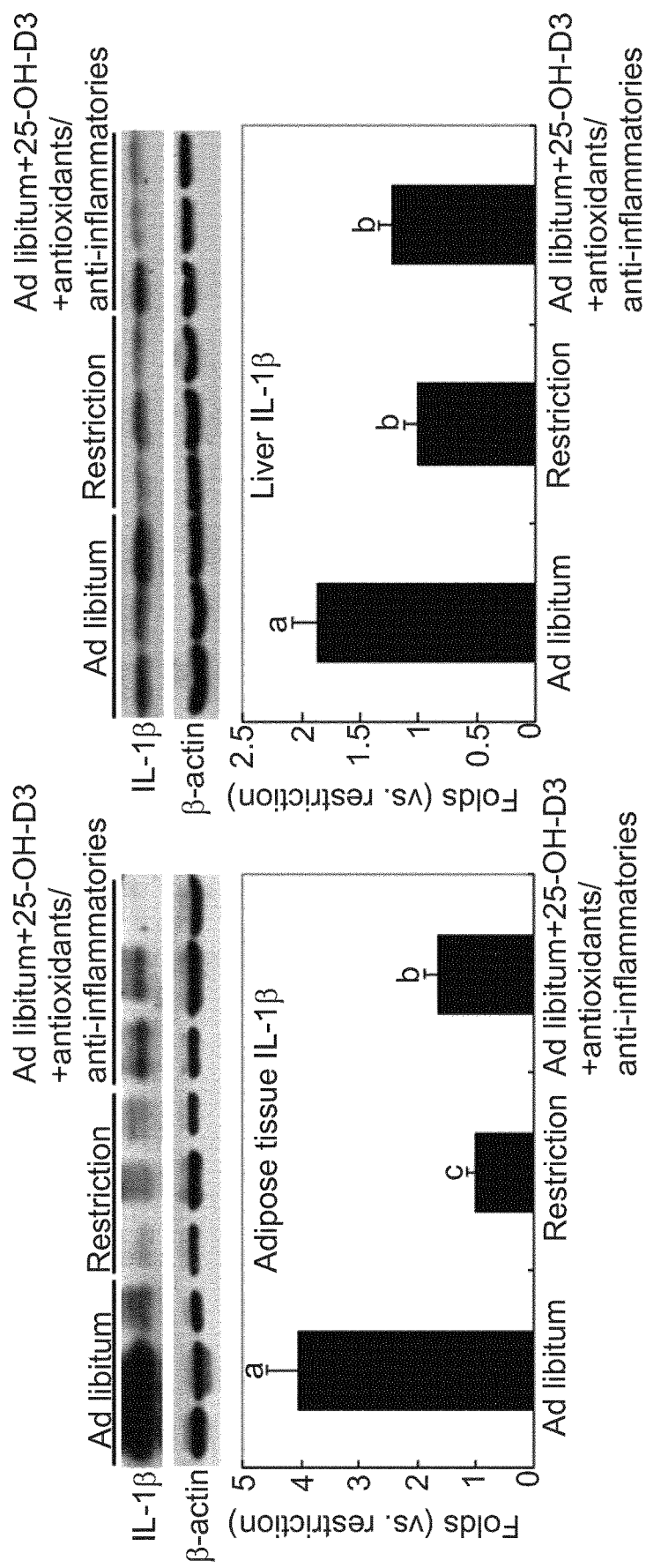
FIG. 2 shows tissue interleukin-1β contents and plasma IL-6 levels of broiler breeder hens in response to ad libitum feed intake in combination with 25-OH D3 and antioxidants/anti-inflammatories. Tissues and blood samples were collected after 10 weeks of the feeding trial. Means with different superscript letters are significantly different (P<0.05), n=3.

25-OH D3 and Antioxidants/Anti-Inflammatories Depressed Tissue Proinflammatory IL-1β Production and Plasma IL-6 Concentrations in Overfed Broiler Hens Obesity-associated inflammation was ameliorated by dietary 25-OH D3 and antioxidants/anti-inflammatories supplementation as evidenced by suppressed circulating IL-6 levels and IL-1β production in adipose tissue, liver, leg and breast muscle, and heart (FIG. 2).

25-OH D3 and Antioxidants/Anti-Inflammatories Ameliorated Lipotoxicity in Broiler Breeder Hens Fed Ad Libitum A central complication of obesity is the development of insulin resistance, which is when insulin is incapable of eliciting postprandial nutrient storage in its primary target tissues, skeletal muscle and liver. Without wishing to be bound by theory, it appears that two probable mechanisms may explain how increased adipose stores affect overall insulin sensitivity throughout the body, contributing to the down regulation of insulin signaling in peripheral tissues. Firstly, the delivery of nutrients to cells or tissues is in excess of their storage capacities and thus this leads to the generation of metabolites that inhibit insulin action. Of particular importance, lipid derivatives, such as triacylglycerol and ceramide, have been shown to inhibit specific insulin signaling intermediates, thus blocking postprandial glucose uptake and/or glycogen synthesis. In the case of broiler breeder females being fed ad libitum, the persistent accumulation of these metabolites in peripheral tissues likely contributes to a sustained state of insulin resistance throughout the hen and of lipotoxic development. Secondly, increased adiposity induces a chronic inflammatory state characterized by elevated circulating levels of proinflammatory cytokines produced from adipocytes or from macrophages infiltrating the fat pad. These inflammatory mediators have been shown to antagonize insulin signaling directly, and also to induce catabolic processes, thus further increasing the delivery of nutrient metabolites to insulin-responsive organs.

Overall, excess supply of glucose leading to the formation of excess saturated fatty acids and therefore accumulation of lipids in non-adipose tissues elevates the cellular levels of-active lipids (sphingolipids) that inhibit the signaling pathways implicated in metabolic regulation together with activated inflammatory responses and lipotoxic development. In particular, ceramide is a putative intermediate linking both excess nutrients (i.e., saturated fatty acids) and inflammatory cytokines to the induction of insulin resistance. Moreover, ceramide is toxic in a variety of different cell types and is capable of damaging the heart, pancreas and vasculature. Moreover, 25-hydroxy D3 and antioxidants/anti-inflammatories were effective in ameliorating the deleterious effect of metabolic and endocrine dysregulations and pro-inflammatory responses resulting from increased adiposity occurring in broiler breeder hens fed to satiation.

25-OH D3 and Antioxidants/Anti-Inflammatories Ameliorate Cardiac Morbidities, Ascites, and Inflammation in Overfed Broiler Hens The heart may become dysfunctional due to excess lipid accumulation. That ad libitum feeding promoted triglyceride accumulation in the heart suggested that increased cardiac fatty acid availability is adaptively esterified into triglyceride. In addition, ceramide content of the heart was also increased as a result of ad libitum feeding. Ceramide is a cardiotoxin in lipotoxic cardiomyopathy, which elicited inflammatory responses as evidenced by more cardiac infiltration of immune cells. (Table 9).

TABLE 8

25-OH D3 and antioxidants/anti-inflammatories on cardiac responses of ad libitum-fed broiler breeder hens

|  | Restricted feeding | Ad libitum feeding | Ad libitum feeding + 25-OH-D3 + antioxidants + anti-inflammatories | Pooled SEM[1] |
|---|---|---|---|---|
| Heart weight (g) | 14.5$^b$ | 19.2$^a$ | 17.3$^a$ | 1.8 |
| Heart/body weight (%) | 0.40 | 0.47 | 0.43 | 0.17 |
| Heart septum (HS) weight (g) | 2.73 | 3.01 | 2.83 | 0.57 |
| HS weight/heart weight (%) | 18.7 | 14.6 | 15.7 | 3.9 |

TABLE 8-continued

25-OH D3 and antioxidants/anti-inflammatories on cardiac responses of ad libitum-fed broiler breeder hens

|  | Restricted feeding | Ad libitum feeding | Ad libitum feeding + 25-OH-D3 + antioxidants + anti-inflammatories | Pooled SEM[1] |
|---|---|---|---|---|
| Right atrium (RA) wall weight (g) | 1.20$^b$ | 1.97$^a$ | 1.72$^{ab}$ | 0.38 |
| RA wall weight/heart weight (%) | 8.2 | 9.6 | 9.6 | 1.9 |
| Right ventricle (RV) wall weight (g) | 0.95$^b$ | 1.51$^a$ | 1.73$^a$ | 0.27 |
| RV wall weight/heart weight (%) | 6.3$^b$ | 7.5$^{ab}$ | 9.4$^a$ | 1.5 |
| Left atrium (LA) wall weight (g) | 1.17$^b$ | 2.26$^a$ | 2.02$^a$ | 0.43 |
| LA wall weight/heart weight (%) | 12.2 | 11.1 | 10.9 | 3.1 |
| Left ventricle (LV) wall weight (g) | 3.78$^b$ | 4.45$^a$ | 4.65$^a$ | 0.34 |
| LV wall weight/heart weight (%) | 25.5$^a$ | 21.7$^b$ | 25.8$^{ab}$ | 2.4 |
| Incidence of transudate within pericardium (heart/total) | 1/7 | 5/10 | 3/10 |  |
| Incidence of heart ventricle dilation (heart/total) | 1/7 | 6/10 | 3/10 |  |
| Incidence of ascites (hen/total) | 0/7 | 3/10 | 1/10 |  |
| Cardiac immune cell count (cells/mm2) | 97.9$^a$ | 127.7$^a$ | 57.7$^b$ | 32.4 |

$^{a-b}$Within a row, means without a common superscript differ (P < 0.05).
[1]Pooled standard error of the mean.

Cardiac hypertrophy represents clinically an adaptive response to increased workload on the heart. However, cardiac responses to neural and hormonal factors can also incite hypertrophic changes independent of increases in afterload or vascular resistance. Fuel overloading-induced cardiac compensatory growth occurred in broiler breeder hens (Table 8). Cardiac hypertrophy may become maladaptive and eventually develop into pathological conditions, leading to heart failure. These results supported the fact that lipotoxic development and hypertrophic growth in the heart tend to elicit inflammatory responses.

Figure 3:
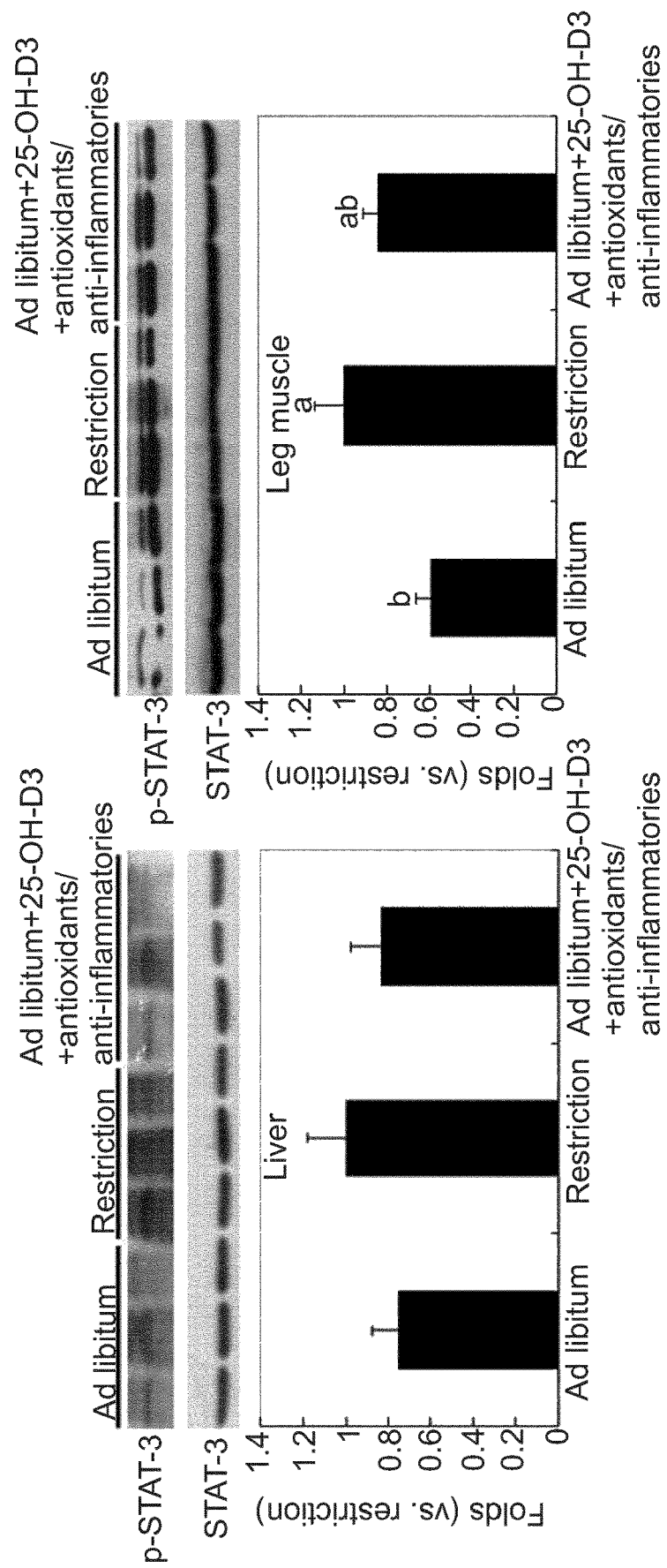
FIG. 3. shows tissue STAT-3 activation of broiler breeder hens in response to ad libitum feed intake in combination with 25-OH D3 and antioxidants/anti-inflammatories inclusion. Tissues and blood samples were collected after 10 weeks of the feeding trial. Means with different superscript letters are significantly different (P<0.05), n=3.
Figure 4:
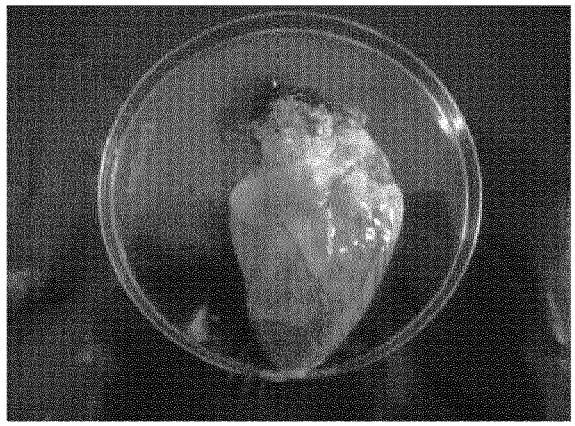
FIGS. 4-6 show pictures taken during the necropsy of broiler hens in response to ad libitum feed intake in combination with 25-OH D3 and antioxidants/anti-inflammatories inclusion. Hens were necropsied after 10 weeks of the feeding trial.
Figure 4:
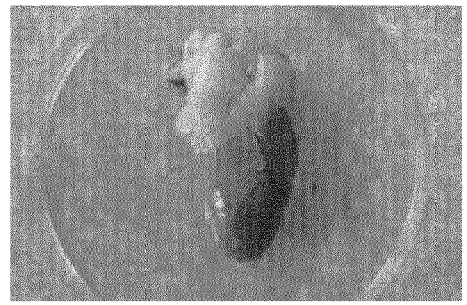
Figure 4:
Figure 4:
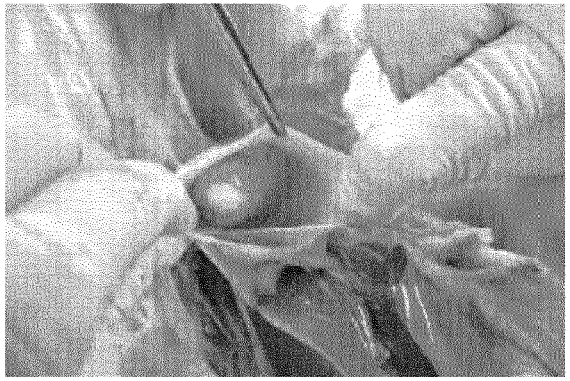
Figure 4:
Figure 4:
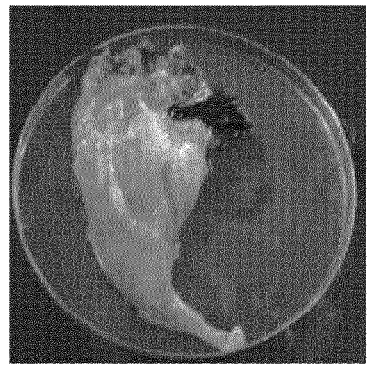
Figure 5:
Figure 5:
Figure 5:
Figure 5:
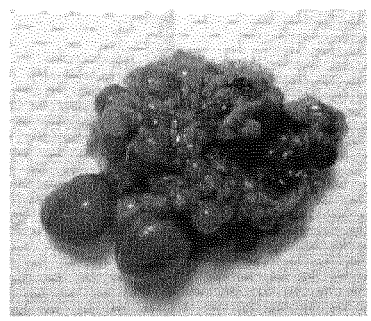
Figure 5:
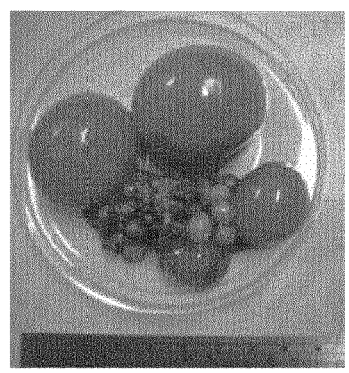
Figure 6:
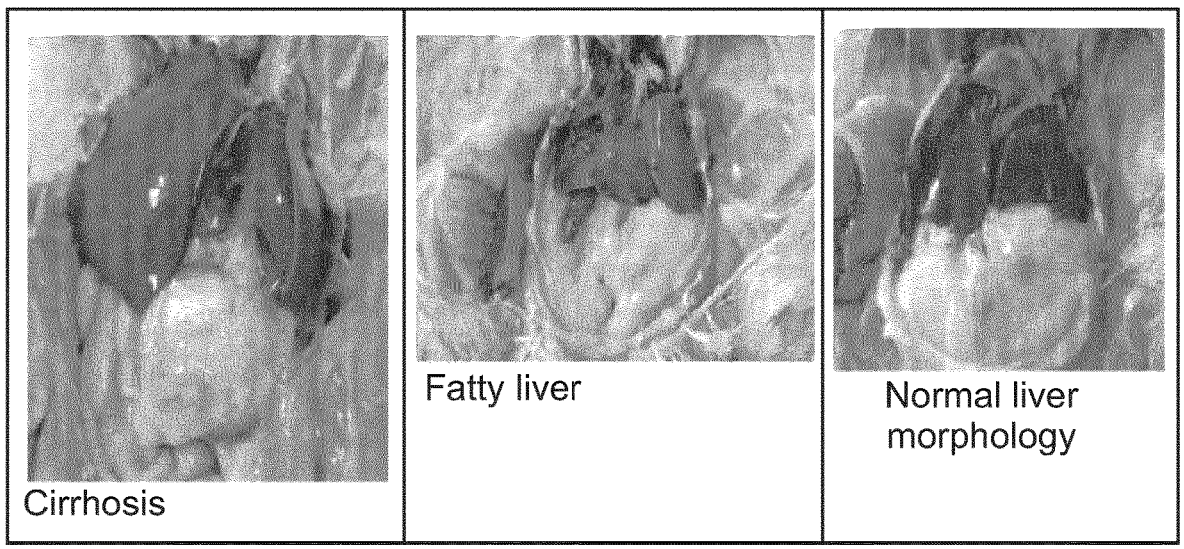

The cardioprotective role of phosphorylated STAT-3 (signal transducer and activator of transcription 3) is becoming increasingly clear in recent years. Interestingly, combined 25-OH D3 and antioxidants/anti-inflammatories induced greater activation of STAT-3 (i.e., phosphorylation of STAT-3) in the heart than restricted-fed breeder hens (FIG. 3), with the lowest activation being observed in ad libitum-fed broiler breeder hens. The incidence of transudate fluid within pericardium, heart ventricle dilation and ascites was alleviated in ad-libitum-fed breeder hens when supplemented with combined 25-hydroxy D3 and antioxidants/anti-inflammatories.

Example 3

Premixes

Table 9, below, presents some of the final dose ranges of the composition of this invention to be added to the feed.

| Vitamin | Unit | Ranges per kg feed | Low per kg feed | Medium per kg feed | High per kg feed |
|---|---|---|---|---|---|
| 25-OH-D3 | mcg | 15-200 | 35 | 69 | 150 |
| Vit E | mg | 40-400 | 80 | 150 | 300 |
| Canthaxanthin | mg | 1-15 | 3 | 6 | 12 |
| Vit C | mg | 40-400 | 100 | 150 | 300 |

Table 10, below presents the quantity of premix dosed per 1 kg feed:

| Vitamin | Unit | 0.3 g premix | 0.6 g premix | 1 g premix | 1.8 g premix | 2 g premix |
|---|---|---|---|---|---|---|
| 25-OH-D3 | mg | 0.0207 | 0.0414 | 0.069 | 0.1242 | 0.138 |
| E | mg | 45 | 90 | 150 | 270 | 300 |
| Canthaxanthin | mg | 1.8 | 3.6 | 6 | 10.8 | 12 |
| C | mg | 45 | 90 | 150 | 270 | 300 |

TABLE 11

1 gram premix can be made with the following ingredients:

| Vitamin | Unit | 1 g premix |
|---|---|---|
| 25-OH-D3 | mg | 0.069 |
| Vit E | mg | 150 |
| Canthaxanthin | mg | 6 |
| Vit C | mg | 150 |
| Carrier and others | mg | to 1000 mg or 1 g |

Example 4

Cardio-Myopathy Trial

Materials and Methods

A total of thirty 45-week-old broiler breeder hens (ROSS 308) were obtained from a commercial flock for the study. A basal broiler breeder laying diet was formulated as shown in Table 12. The calculated nutrient composition is shown in Table 13.

TABLE 12

Ingredient composition of the basal broiler breeder laying diets.

| Composition | %, w/w |
|---|---|
| Corn | 66.9 |
| Soybean meal | 22.2 |
| Oil fat | 1.67 |
| Calcium carbonate (ground oyster shell) | 6.36 |
| Dicalcium phosphate | 1.8 |
| Salt | 0.08 |
| Choline-Cl (70%) | 0.1 |
| Mineral premix[1] | 0.1 |
| Cooper sulfate | 0.05 |
| Vitamin premix[2] | 0.1 |

[1]Mineral premix provided (per kg of diet for treatment groups 1, 2 and 3): Cu, 18 mg; I, 1.1 mg; Fe, 80 mg; Mn, 150 mg; Zn, 125 mg; and Se, 0.25 mg.
[2]Refer to Table 13, below for further detail.

TABLE 13

Vitamin premix composition (provided per kg of diet)

| Vitamin | Treatments 1 and 3<br>1 = restricted feeding<br>3 = ad libitum feeding | Treatments 2 and 4<br>2 = restricted feeding + 25-OH-D3 + antioxidants/anti-inflammatories<br>4 = ad libitum feeding + 25-OH-D3 + antioxidants/anti-inflammatories |
|---|---|---|
| A (IU) | 10000 | 12000 |
| D3 (IU) | 2500 | 3000 |
| E (mg) | 100 | 150 |
| K3 (mg) | 3 | 5 |
| B1 (mg) | 3 | 5 |
| B2 (mg) | 8 | 14 |
| B6 (mg) | 6 | 8 |
| B12 (mg) | 0.03 | 0.03 |
| Niacin (mg) | 60 | 120 |
| Pantothenic acid (mg) | 18 | 30 |
| Folic acid (mg) | 1 | 4 |
| Biotin (mg) | 0.2 | 0.4 |
| C (mg) | 0 | 150 |
| 25-OH-D3 (mcg) | 0 | 69 |
| Canthaxanthin (mg) | 0 | 6 |

TABLE 14

Calculated nutrient composition (%) of the basal broiler breeder laying diets.

| Composition | %, w/w |
|---|---|
| Crude protein | 16 |
| Crude fat | 4.2 |
| Calcium | 3.1 |
| Potassium | 0.44 |
| Sodium | 0.16 |
| Total phosphorus | 0.64 |
| Total ME | 2910 kcal/kg |

Diet was supplemented with or without Hy•D® at 69 mcg 25-OH-D3/kg diet in combination with antioxidants (ascorbic acid, canthaxanthin) and enriched levels of selected vitamins. Hens were randomly allocated to treatment groups according to feeding regimen (restricted and ad libitum) as follows:

1. Basal diet—restricted feeding (140 g/day)
2. Basal diet—restricted feeding+Hy•D® (25-OH-D3 at 69 mcg/kg diet)+antioxidants/anti-inflammatories
3. Basal diet—ad libitum feeding
4. Basal diet—ad libitum feeding+Hy•D® (25-OH-D3 at 69 mcg/kg diet)+antioxidants/anti-inflammatories Results:

TABLE 15

Effect of dietary supplementation of 25-OH-D3+antioxidants/anti-inflammatories on egg production of broiler hens with restricted or ad libitum feed intake.

| | Restriction | | Restriction + 25-OH-D3+ antioxidant/anti-inflammatories | | Ad libitum | | Ad libitum + 25-OH-D3+ antioxidant/anti-inflammatories | |
|---|---|---|---|---|---|---|---|---|
| | Whole flock (n = 68) | Dead bird flock (n = 19) | Whole flock (n = 70) | Dead bird flock (n = 11) | Whole flock (n = 80) | Dead bird flock (n = 58) | Whole flock (n = 79) | Dead bird flock (n = 47) |
| PROD | 51.4 ± 2.5$^a$ | 47.2 ± 1.9$^a$ | 51.3 ± 2.7$^a$ | 40.2 ± 1.8$^b$ | 32.0 ± 2.9$^b$ | 43.4 ± 1.7$^{ab}$ | 34.8 ± 2.7$^b$ | 45.8 ± 2.1$^{ab}$ |
| YIELD | 129.0 ± 5.5$^b$ | 47.9 ± 2.5$^b$ | 143.2 ± 5.7$^a$ | 33.3 ± 1.9$^b$ | 41.1 ± 5.3$^d$ | 41.5 ± 2.1$^b$ | 54.7 ± 5.9$^c$ | 41.1 ± 2.0$^b$ |

PROD = Egg production rate (eggs/day/hen, %);
YIELD = Egg yield (eggs/hen)
Results were expressed with mean ± SEM.
Means with different superscript letters are significantly different within the same flock (P < 0.05).

Figure 7:
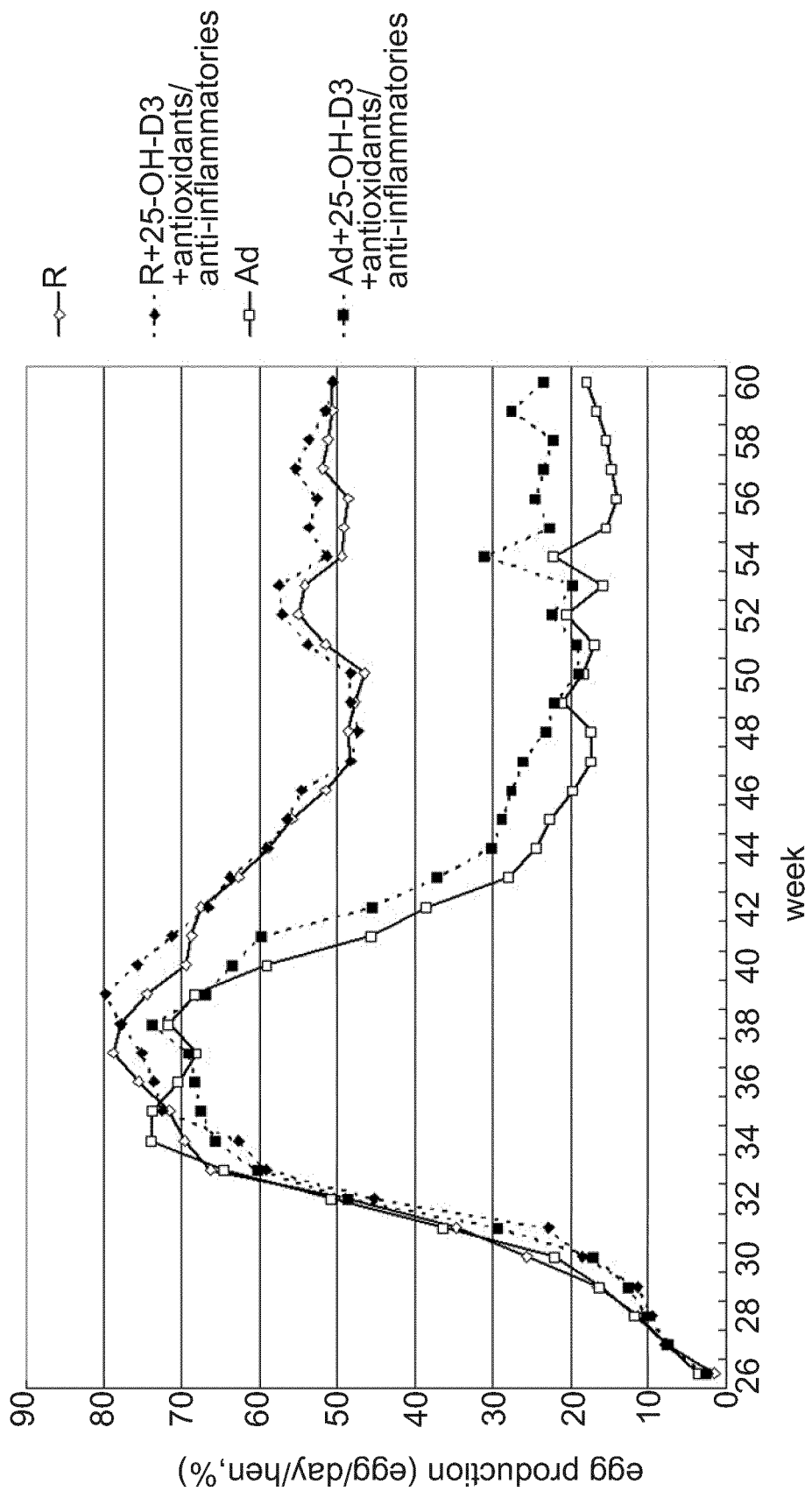
FIG. 7 shows the effect of dietary supplementation of 25-OH-D3+antioxidants/anti-inflammatories on egg production of broiler hens with restricted or ad libitum feed intake.

FIG. 7 shows the effect of dietary supplementation of 25-OH-D3+antioxidants/anti-inflammatories on egg production of broiler hens with restricted or ad libitum feed intake. From TABLE 15 and FIG. 7, it can be concluded that:
1. 25-OH-D3+antioxidants/anti-inflammatories improved total egg yield by promoting survival.
2. In dead birds, 25-OH-D3+antioxidants/anti-inflammatories had no effect on egg yield and egg production rate in bird fed ad libitum, but decreased egg yield and egg production rate in restricted birds. In the whole flock, however, 25-OH-D3+antioxidants/anti-inflammatories increased egg yield but not egg production rate.
3. These results suggested that 25-OH-D3+antioxidants/anti-inflammatories accelerated the progression into death in restricted birds that are susceptible to sudden death, and thus acting as a flock culler to exclude the sudden death-susceptible birds for longer survival and thereby reduced the flock maintenance cost.

TABLE 16

Effect of dietary supplementation of 25-OH-D3 + antioxidants/anti-inflammatories on mortality of broiler hens with restricted or ad libitum feed intake and body characteristics of the dead hens

| | Restriction (n = 19) | Restriction + 25-OH-D3 + antioxidant/anti-inflammatories (n = 11) | Ad libitum (n = 58) | Ad libitum ++ 25-OH-D3 + antioxidant/anti-inflammatories (n = 47) |
|---|---|---|---|---|
| Mortality (dead birds of the total) | 19/68 (26.47%) | 11/70 (15.71%) | 58/80 (72.5%) | 47/79 (59.49%) |
| Body weight of the dead birds (kg) | 3.91 ± 0.090 $^c$ | 4.01 ± 0.084$^{bc}$ | 4.07 ± 0.083 $^b$ | 4.37 ± 0.082 $^a$ |
| Liver weight of the dead birds (g) | 89.10 ± 6.79 $^b$ | 99.27 ± 7.92 $^{ab}$ | 105.52 ± 5.48$^a$ | 106.70 ± 4.68 $^a$ |
| Relative liver weight of the dead birds (g/100 g BW) | 2.28 ± 0.0016 $^d$ | 2.47 ± 0.0020 $^b$ | 2.59 ± 0.0011$^a$ | 2.44 ± 0.0009$^c$ |
| Abdominal fat weight of the dead birds (g) | 60.45 ± 4.56 $^b$ | 68.54 ± 6.05 $^b$ | 148.64 ± 8.45$^c$ | 133.54 ± 9.44$^a$ |
| Relative abdominal fat weight of the dead birds (g/100 g BW) | 1.55 ± 0.0013 $^d$ | 1.71 ± 0.0016 $^c$ | 3.65 ± 0.0014 $^a$ | 3.06 ± 0.0009 $^b$ |
| Heart weight of the dead birds (g) | 18.12 ± 0.81 $^c$ | 19.93 ± 0.87$^b$ | 23.66 ± 0.96$^a$ | 22.29 ± 0.86$^a$ |

TABLE 16-continued

Effect of dietary supplementation of 25-OH-D3 + antioxidants/anti-inflammatories on mortality of broiler hens with restricted or ad libitum feed intake and body characteristics of the dead hens

|  | Restriction (n = 19) | Restriction + 25-OH-D3 + antioxidant/ anti-inflammatories (n = 11) | Ad libitum (n = 58) | Ad libitum ++ 25-OH-D3 + antioxidant/ anti-inflammatories (n = 47) |
|---|---|---|---|---|
| Relative heart weight of the dead birds (g/100 g BW) | 0.46 ± 0.00023[c] | 0.50 ± 0.00021[b] | 0.58 ± 0.00024[a] | 0.51 ± 0.00018[b] |

Results were expressed with mean ± SEM.
Means with different superscript letters are significantly different ($P < 0.05$)

Figure 8:
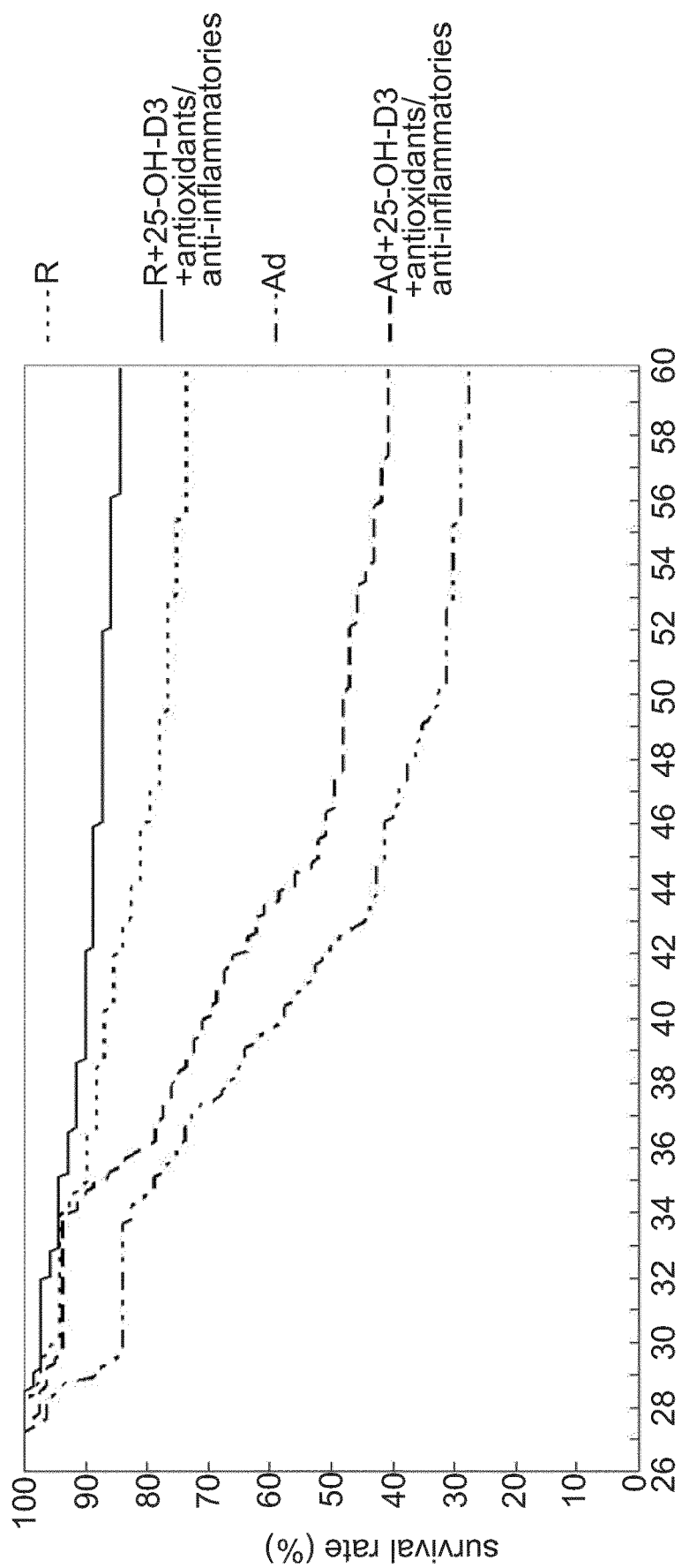
FIG. 8 shows the effect of dietary supplementation of 25-OH-D3+antioxidants/anti-inflammatories on the survival rate of broiler hens with restricted or ad libitum feed intake.

FIG. 8 shows the effect of dietary supplementation of 25-OH-D3+antioxidants/anti-inflammatories on the survival rate of broiler hens with restricted or ad libitum feed intake Conclusions and Annotations from Table 16 and FIG. 8:
1. 25-OH-D3+antioxidants/anti-inflammatories improved bird survival rate.
2. In birds fed ad libitum, dead birds with 25-OH-D3+ antioxidants/anti-inflammatories had higher body weight, but lower relative liver, abdominal fat, and heart weight, suggesting that most excessive fuels may be partitioned to the muscle, and thereby, adaptive hypertrophic growth of the heart for increased pumping function cannot meet the need of oxygen supply for higher growth rate (muscle) and thus may provoke cardiac arrhythmia and failure.

TABLE 17

Effect of dietary supplementation of 25-OH-D3 + antioxidants/anti-inflammatories on carcass characteristics at age of 35 and 50 wks of broiler hens with restricted or ad libitum feed intake

|  | Restriction (n = 6) | Restriction + 25-OH-D3 + antioxidant/ anti-inflammatories (n = 6) | Ad libitum (n = 6) | Ad libitum + 25-OH-D3 + antioxidant/ anti-inflammatories (n = 6) |
|---|---|---|---|---|
| Body wt (kg): | | | | |
| at 35 wks | 3.57 ± 0.19[b] | 3.66 ± 0.15[b] | 4.32 ± 0.27[a] | 4.36 ± 0.33[a] |
| at 50 wks | 3.78 ± 0.21[b] | 3.83 ± 0.23[b] | 4.62 ± 0.34[a] | 4.71 ± 0.38[a] |
| Liver wt(g): | | | | |
| at 35 wks | 55.35 ± 4.42[b] | 57.37 ± 2.27[b] | 98.45 ± 4.76[a] | 83.37 ± 4.17[b] |
| at 50 wks | 58.67 ± 3.84[b] | 59.75 ± 4.67[b] | 72.56 ± 5.14[a*] | 68.45 ± 3.42[b*] |
| Relative liver wt (g/100 g BW, %): | | | | |
| at 35 wks | 1.55 ± 0.06[d] | 1.57 ± 0.11[b] | 2.28 ± 0.10[a] | 1.91 ± 0.09[b] |
| at 50 wks | 1.55 ± 0.05 | 1.56 ± 0.14 | 1.57 ± 0.13* | 1.45 ± 0.07* |
| Abdominal fat wt of the dead birds (g): | | | | |
| at 35 wks | 47.63 ± 2.16[c] | 50.57 ± 3.64[c] | 123.84 ± 9.84[a] | 95.47 ± 8.12[b] |
| at 50 wks | 51.24 ± 2.38[c] | 53.12 ± 2.57[c] | 147.62 ± 8.55[c*] | 112.47 ± 9.01[c] |
| Relative abdominal fat wt (g/100 g BW, %): | | | | |
| at 35 wks | 1.35 ± 0.11[c] | 1.38 ± 0.06[c] | 2.86 ± 0.0[a] | 2.19 ± 0.03[b] |
| at 50 wks | 1.36 ± 0.12[c] | 1.39 ± 0.50[c] | 3.20 ± 0.06[a*] | 2.39 ± 0.08[b*] |
| Heart wt (g): | | | | |
| at 35 wks | 12.69 ± 0.38[b] | 12.09 ± 0.31[b] | 17.33 ± 0.65[a] | 17.76 ± 0.70[a] |
| at 50 wks | 14.12 ± 0.41[b] | 13.88 ± 0.0.36[b] | 22.21 ± 0.71[a*] | 20.88 ± 0.73[a*] |

TABLE 17-continued

Effect of dietary supplementation of 25-OH-D3 + antioxidants/anti-inflammatories on carcass characteristics at age of 35 and 50 wks of broiler hens with restricted or ad libitum feed intake

|  | Restriction (n = 6) | Restriction + 25-OH-D3 + antioxidant/anti-inflammatories (n = 6) | Ad libitum (n = 6) | Ad libitum + 25-OH-D3 + antioxidant/anti-inflammatories (n = 6) |
|---|---|---|---|---|
| Relative heart wt (g/100 g BW, %): | | | | |
| at 35 wks | $0.357 \pm 0.024^{b}$ | $0.331 \pm 0.011^{b}$ | $0.401 \pm 0.016^{a}$ | $0.414 \pm 0.046^{ab}$ |
| at 50 wks | $0.374 \pm 0.025^{b}$ | $0.362 \pm 0.024^{b}$ | $0.481 \pm 0.015^{a*}$ | $0.443 \pm 0.024^{ab}$ |

Results were expressed with mean ± SEM.
Means with different superscript letters are significantly different (P < 0.05);
*significant difference vs. age at 35 wks.

The low relative liver weight in ad libitum birds at age of 50 weeks appears to be due to ovarian regression developed and thus decreased estrogen secretion leading to decreased lipid synthesis in the liver for yolk deposition.

Figure 9:
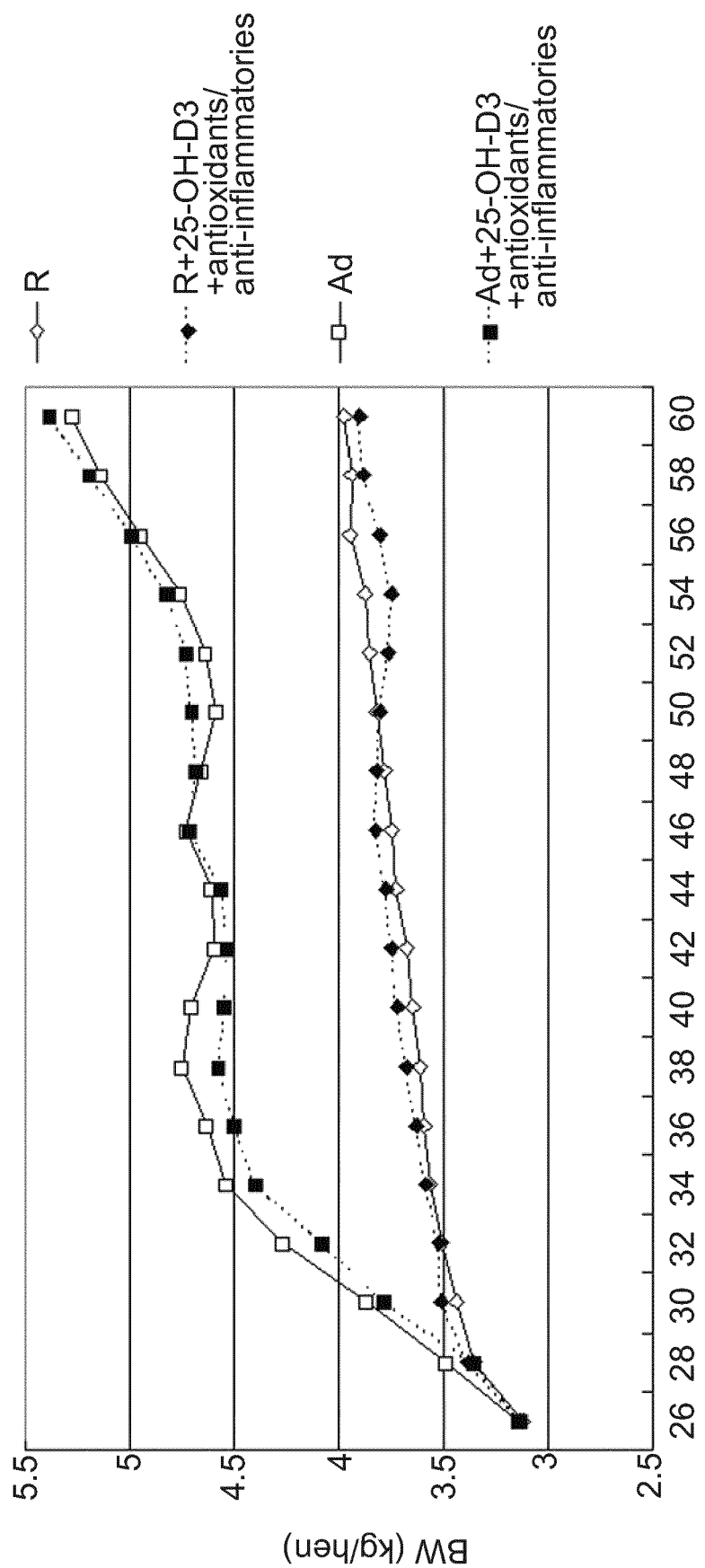
FIG. 9 shows the effect of dietary supplementation of 25-OH-D3+antioxidants/anti-inflammatories on body weight of broiler hens with restricted or ad libitum feed intake.

FIG. 9 shows the effect of dietary supplementation of 25-OH-D3+antioxidants/anti-inflammatories on body weight of broiler hens with restricted or ad libitum feed intake

TABLE 18

Effect of dietary supplementation of 25-OH-D3+antioxidants/anti-inflammatories on the cardiac morbidities of the dead hens with restricted or ad libitum feed intake

|  | Restriction (n = 19) | Restriction + 25-OH-D3+ antioxidant/anti-inflammatories (n = 11) | Ad libitum (n = 58) | Ad libitum + (25-OH-D3+ antioxidant/anti-inflammatories (n = 47) |
|---|---|---|---|---|
| Mortality (dead birds of the total) | 19/68 (26.47%) | 11/70 (15.71%) | 58/80 (72.5%) | 47/79 (59.49%) |
| Cardiac morbidities (birds of the death | | | | |
| 1. hypertrophy | 6/19 | 0/11 | 20/58 | 14/47 |
| 2. ventricle dilation | 3/19 | 3/11 | 16/58 | 10/47 |
| 3. effusion in the pericardial cavity | 6/19 | 0/11 | 26/58 | 15/47 |
| 4. ascites | 2/19 | 0/11 | 7/58 | 5/47 |
| 5. myocardial rupture trauma | 1/19 | 0/11 | 6/58 | 4/47 |
| 1 + 3 | 2/19 | 0/11 | 10/58 | 7/47 |
| 2 + 3 | 2/19 | 1/11 | 11/58 | 6/47 |
| 1 + 4 | 2/19 | 0/11 | 3/58 | 0/47 |
| 3 + 4 | 1/19 | 0/11 | 2/58 | 1/47 |
| 2 + 5 | 0/19 | 0/11 | 3/58 | 1/47 |
| 2 + 3 + 4 | 0/19 | 0/11 | 2/58 | 1/47 |

Results were expressed as a ratio.

Figure 10B:
FIG. 10 is a series of photos showing the gross morphology of the heart of dead hens with dietary supplementation of 25-OH-D3+antioxidants/anti-inflammatories under restricted or ad libitum feed intake.
Figure 10A:
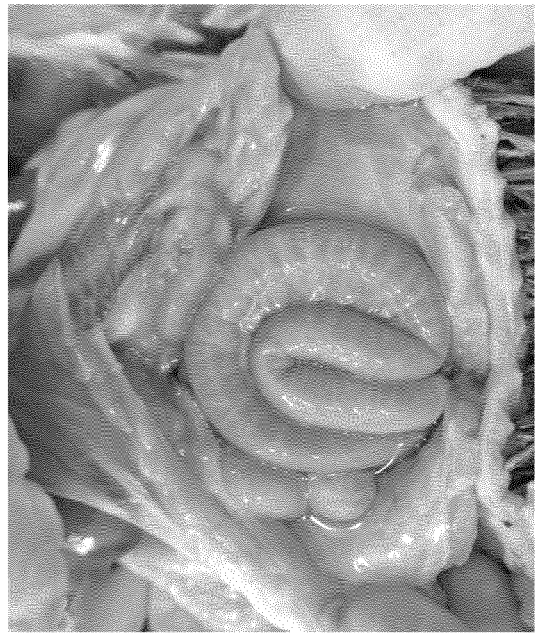
Figure 10C:
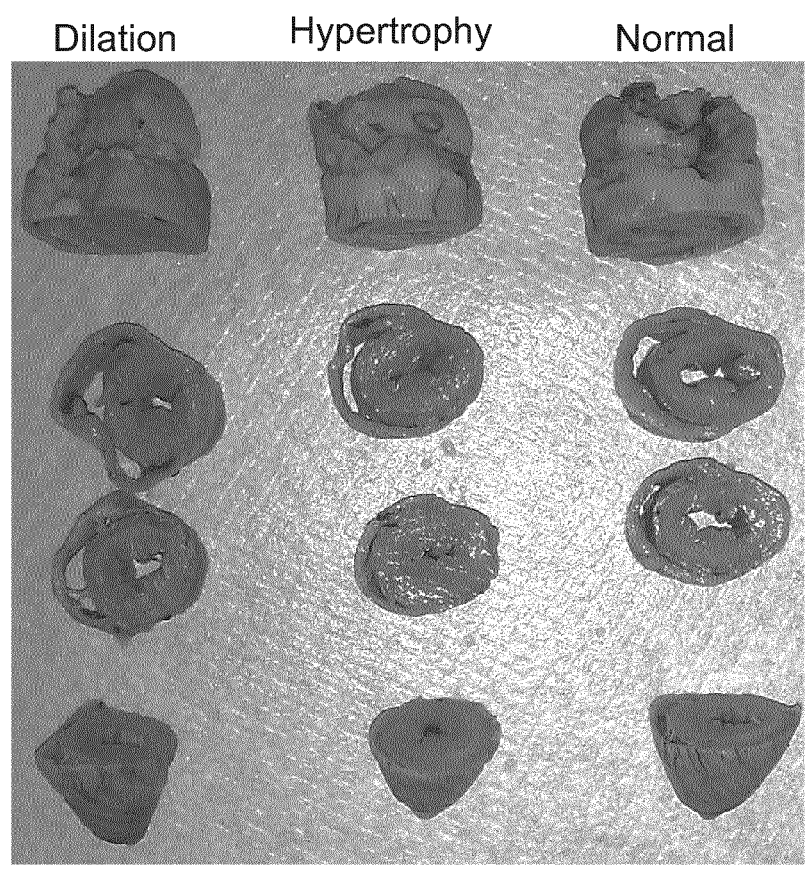
Figure 11C:
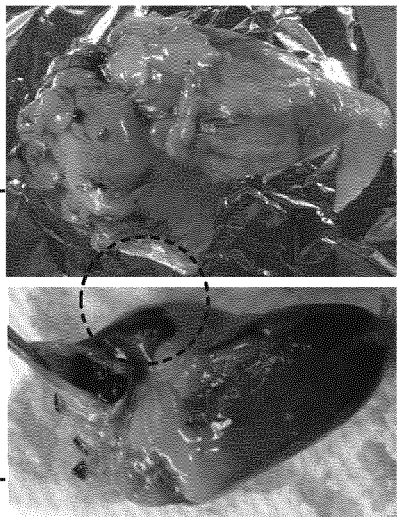
FIG. 11 is a series of photographs showing the gross morphology of the heart of dead hens with dietary supplementation of 25-OH-D3+antioxidants/anti-inflammatories under restricted or ad libitum feed intake
Figure 11F:
Figure 11B:
Figure 11E:
Figure 11A:
Figure 11D:
Figure 11I:
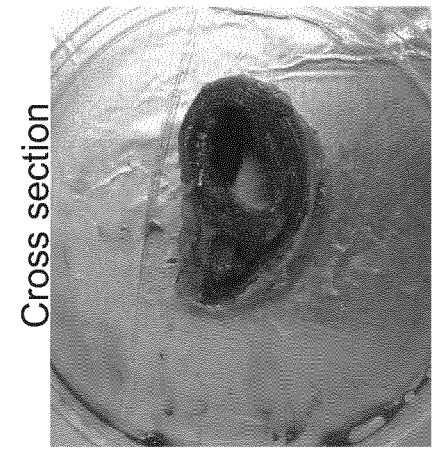
Figure 11H:
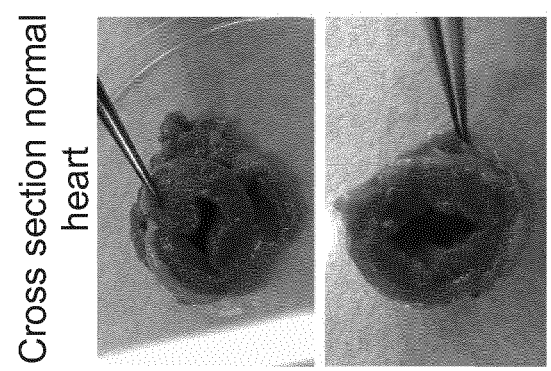
Figure 11G:
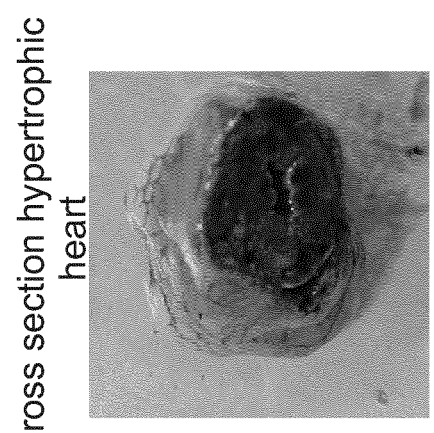

FIGS. 10-11 illustrate the gross morphology of the heart of dead hens with dietary supplementation of 25-OH-D3+antioxidants/anti-inflammatories under restricted or ad libitum feed intake.

Conclusions and Annotations from Tables 17 and 18 and FIGS. 9-11:

1. Ad libitum feeding caused cardiac adaptive hypertrophy, and some of the hypertrophic growth may develop pathologically into ventricle dilation. As a result, the heart requires a higher contractility to maintain pumping function to meet the need of blood supply for oxygen delivery to the peripheral tissues and this may have caused heart failure.

2. 25-OH-D3+antioxidants/anti-inflammatories decreased the incidence of cardiac morbidities (dilation, pericardial effusion, rupture) in the dead birds.

3. In both restricted and ad libitum fed birds, birds with 25-OH-D3+antioxidants/anti-inflammatories exhibited less adaptive hypertrophic growth. This supports the hypothesis that that most excessive fuels may be partitioned to the muscle, and thereby, hypertrophic growth of the heart for increased pumping function cannot meet the need of oxygen supply for higher growth rate (muscle) and thus may provoke cardiac arrhythmia and failure.

TABLE 19

Effect of dietary supplementation of 25-OH-D3 + antioxidants/anti-inflammatories on electrocardiogram (ECG) pattern and arrhythmia of broiler hens with restricted or ad libitum feed intake. See FIGS. 12 and 13 for examples of the EGC patterns.

|  | Restriction (n = 8) | Restriction + 25-OH-D3 + antioxidant/anti-inflammatories (n = 8) | Ad libitum (n = 8) | Ad libitum + 25-OH-D3 + antioxidant/anti-inflammatories (n = 8) |
|---|---|---|---|---|
| ECG pattern A at age of 35 wks | 4/8 | 4/8 | 1/8 | 3/8 |
| ECG pattern B or C at age of 35 wks | 2/8 | 3/8 | 2/8 | 3/8 |
| ECG pattern D, E, F, or G at age of 35 weeks | 2/8 | 1/8 | 5/8 | 2/8 |
| ECG pattern A at age of 50 wks | 3/8 | 4/8 | 0/8 | 2/8 |
| ECG pattern B or C at age of 50 wks | 3/8 | 2/8 | 1/8 | 3/8 |
| ECG pattern D, E, F, or G at age of 50 weeks | 2/8 | 2/8 | 7/8 | 3/8 |

TABLE 19-continued

Effect of dietary supplementation of 25-OH-D3 + antioxidants/anti-inflammatories on electrocardiogram (ECG) pattern and arrhythmia of broiler hens with restricted or ad libitum feed intake. See FIGS. 12 and 13 for examples of the EGC patterns.

|  | Restriction (n = 8) | Restriction + 25-OH-D3 + antioxidant/ anti-inflam- matories (n = 8) | Ad libitum (n = 8) | Ad libitum + 25-OH-D3 + antioxidant/ anti-inflam- matories (n = 8) |
| --- | --- | --- | --- | --- |
| Arrhythmic ECG pattern at age of 35 wks | 0/8 | 0/8 | 2/8 | 1/8 |
| Arrhythmic ECG pattern at age of 50 wks | 1/8 | 1/8 | 4/8 | 2/8 |

Figure 12:
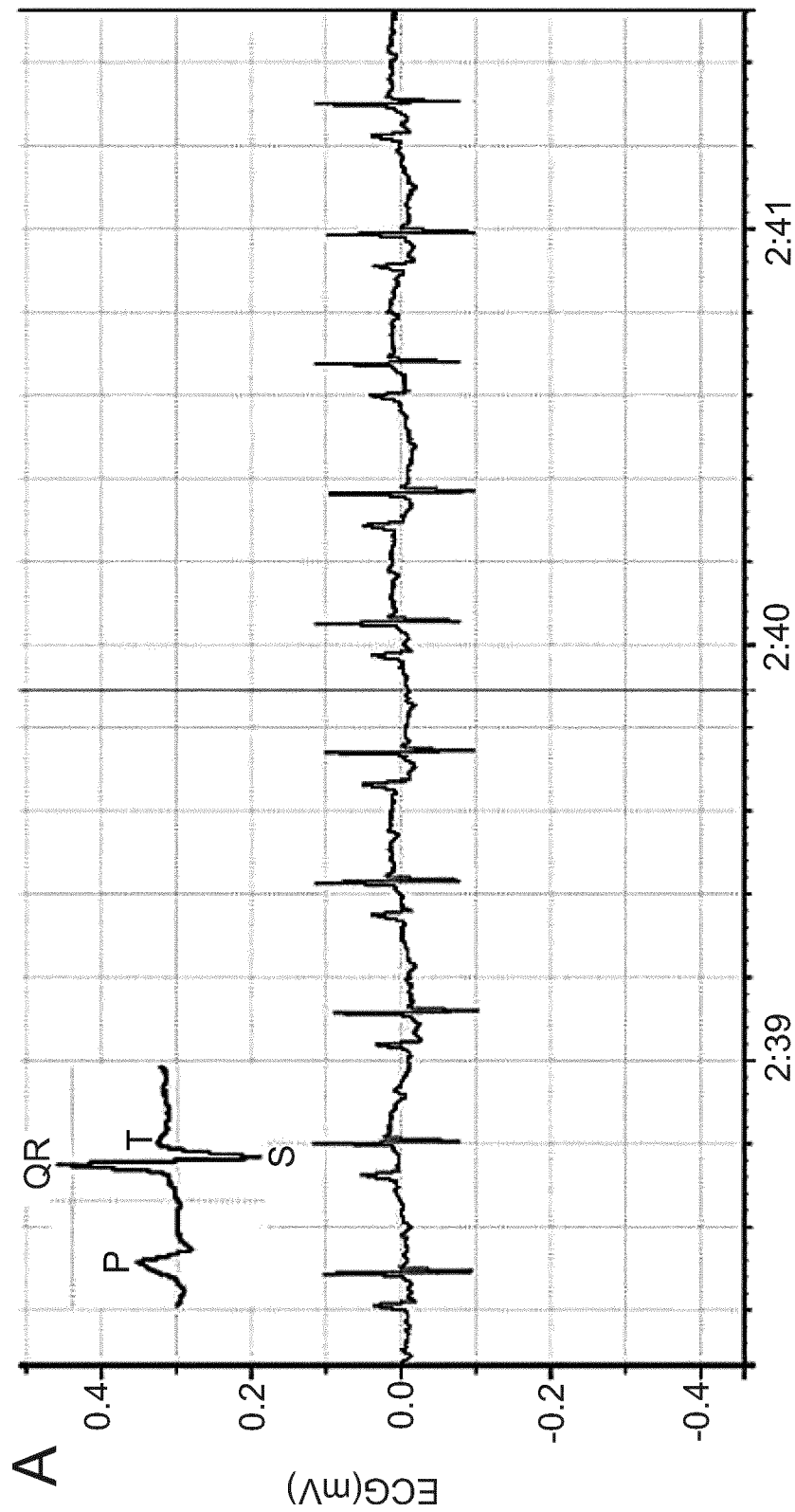
FIG. 12 is a series of electrocardiograms (EGCs) demonstrating the effect of dietary supplementation of 25-OH-D3+antioxidants/anti-inflammatories on EGC of broiler hens with restricted or ad libitum feed intake. The arrows point to irregularities in the patterns.
Figure 13:
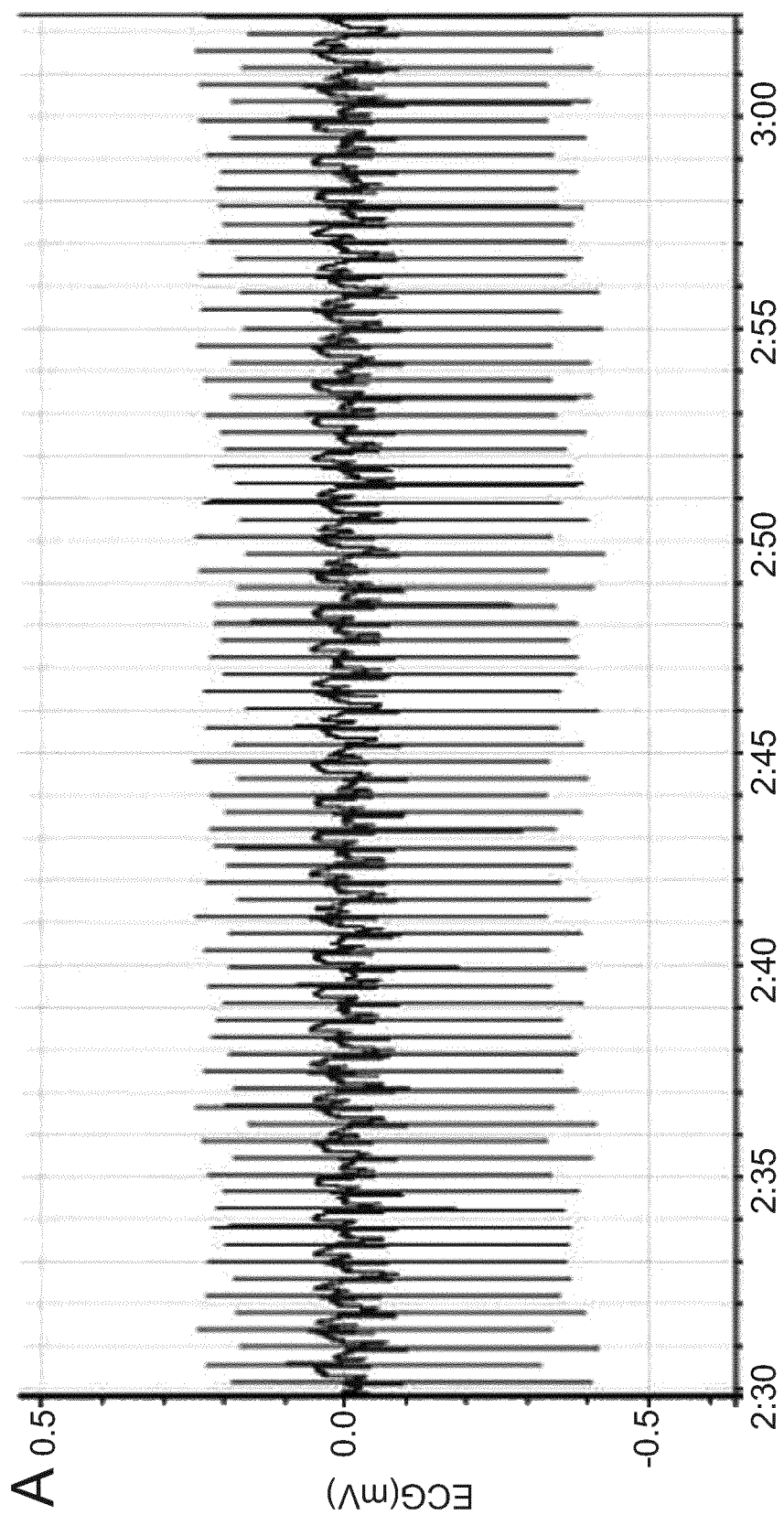
FIG. 13 is a series of EGSs showing the effect of dietary supplementation of 25-OH-D3+antioxidants/anti-inflammatories on arrhythmic ECG pattern of broiler hens with restricted or ad libitum feed intake.

Conclusions and Annotations from Table 19 and FIGS. 12 and 13:
  25-OH-D3+antioxidants/anti-inflammatories decreased irregular incidence of ECG pattern (pattern D to G) and arrhythmia of broiler hens fed ad libitum and ameliorated sudden death induced by cardiac morbidities.

Figure 14:
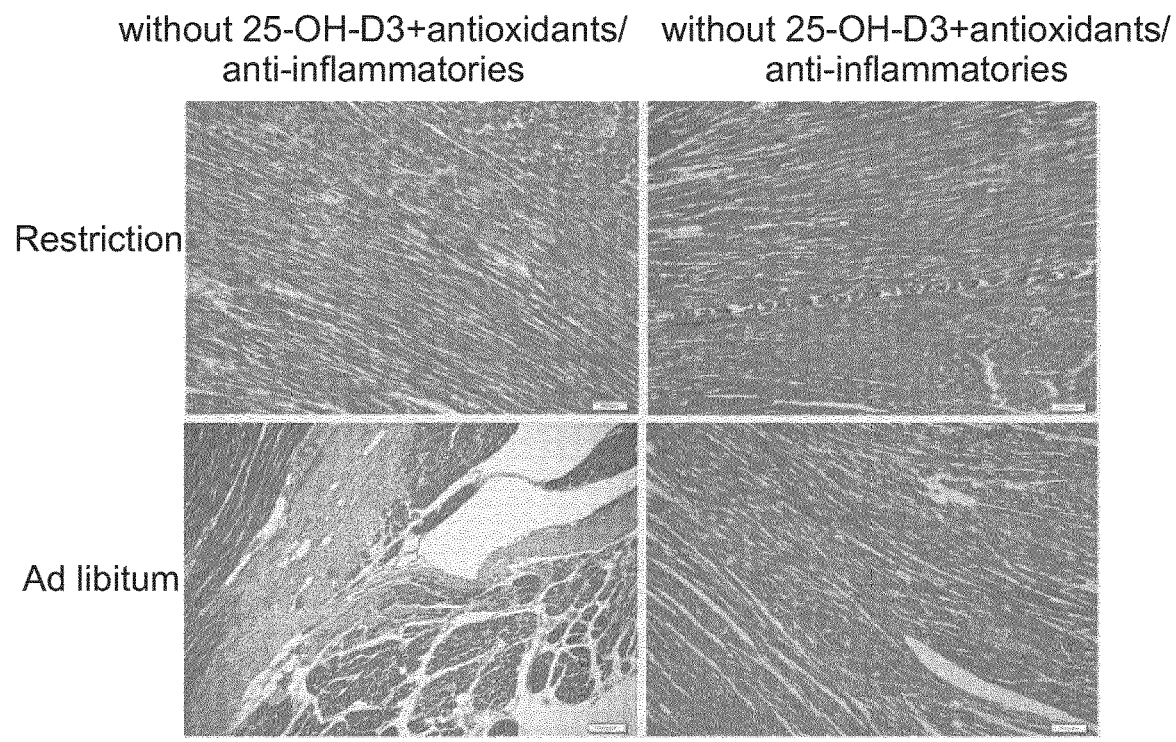
FIG. 14 shows photos and a graph demonstrating the effect of dietary supplementation of 25-OH-D3+antioxidants/anti-inflammatories on cardiac fibrosis of broiler hens with restricted or ad libitum feed intake. (at age of 35 weeks)
Figure 14:
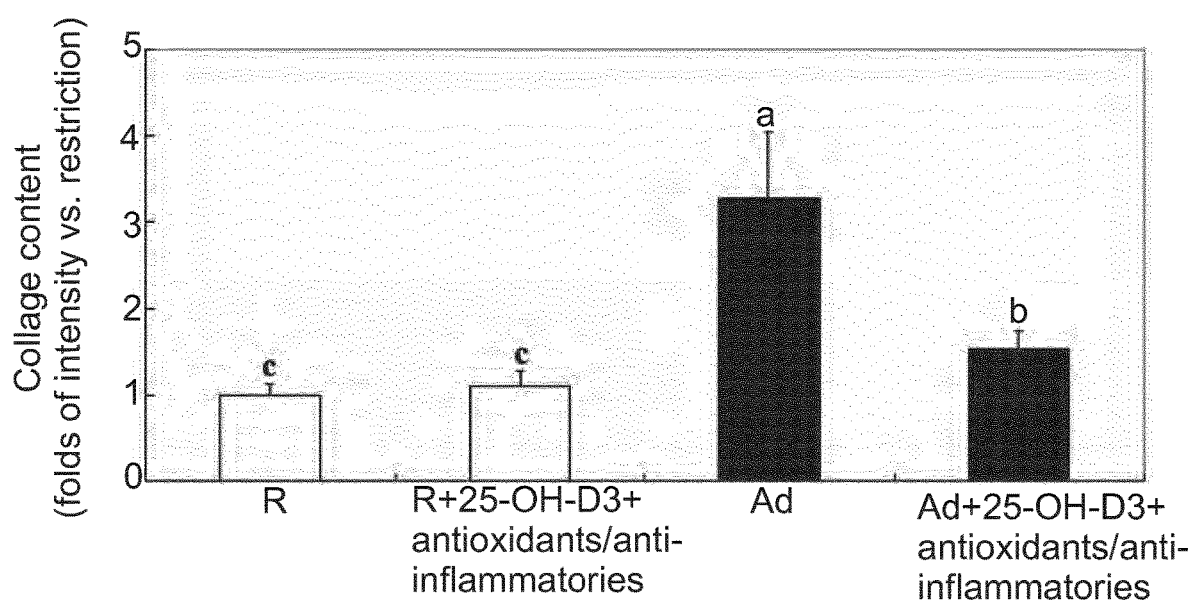

FIG. 14 shows the effect of dietary supplementation of 25-OH-D3+antioxidants/anti-inflammatories on cardiac fibrosis of broiler hens with restricted or ad libitum feed intake. (at age of 35 weeks) Means with different superscript letters are significantly different (P<0.05)

Conclusions and Annotations from FIG. 14
1. 25-OH-D3+antioxidants/anti-inflammatories ameliorated cardiac fibrosis in hens fed ad libitum.

Figure 15:
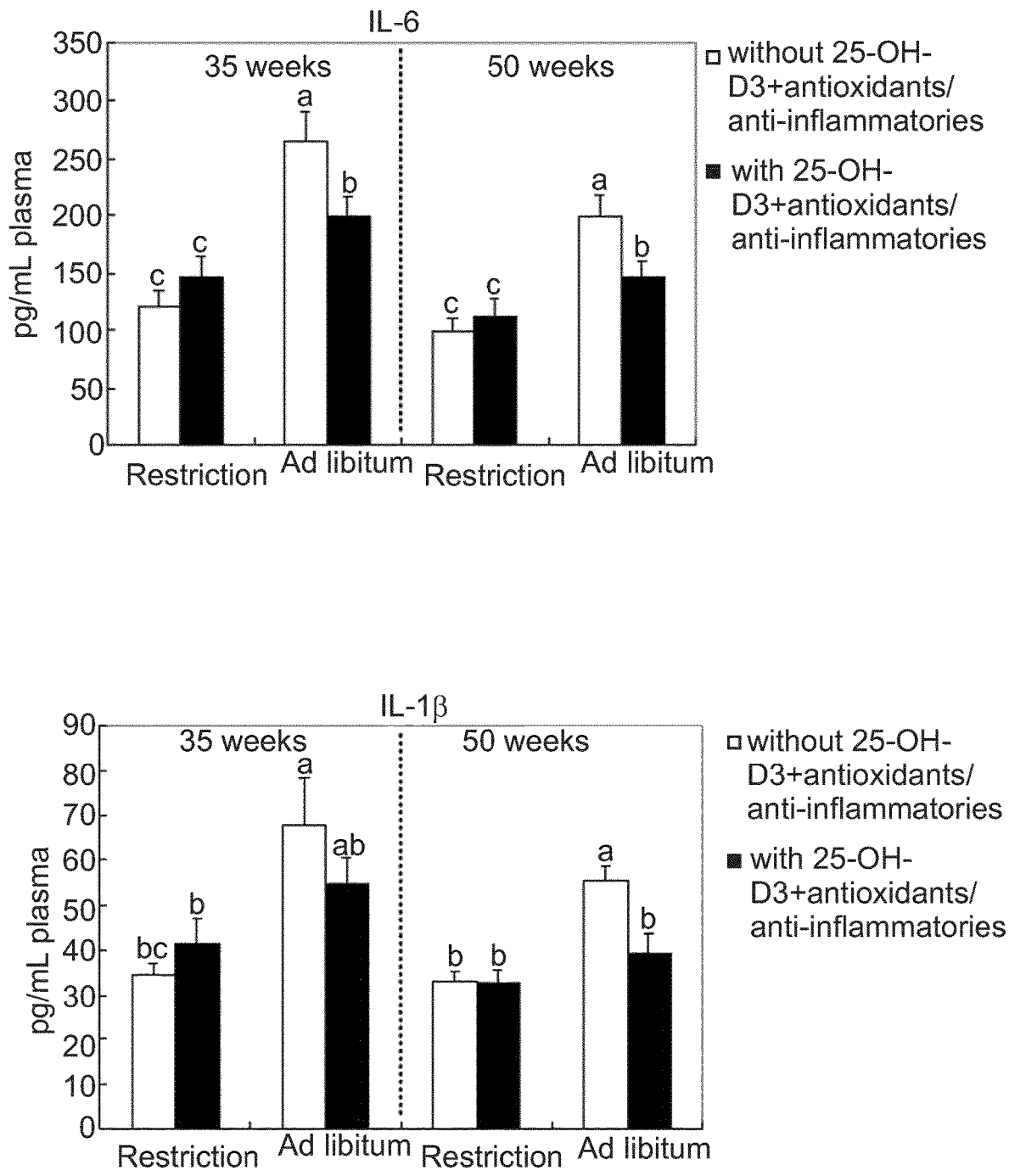
FIG. 15 are graphs showing the effect of dietary supplementation of 25-OH-D3+antioxidants/anti-inflammatories on plasma IL-6 and IL-1β concentration of broiler hens with restricted or ad libitum feed intake.

FIG. 15 shows the effect of dietary supplementation of 25-OH-D3+antioxidants/anti-inflammatories on plasma IL-6 and IL-1β concentration of broiler hens with restricted or ad libitum feed intake. Results were expressed with mean±SEM (n=6). Means with different superscript letters are significantly different (P<0.05)

Conclusions and Annotations from FIG. 15:
  25-OH-D3+antioxidants/anti-inflammatories ameliorated chronic systemic inflammation in hens fed ad libitum.

FIG. 15 shows the effect of dietary supplementation of 25-OH-D3+antioxidants/anti-inflammatories on cardiac cell apoptosis of broiler hens with restricted or ad libitum feed intake. (at age of 35 weeks). Results were expressed with mean±SEM (n=3). Means with different superscript letters are significantly different (P<0.05)

Figure 16:
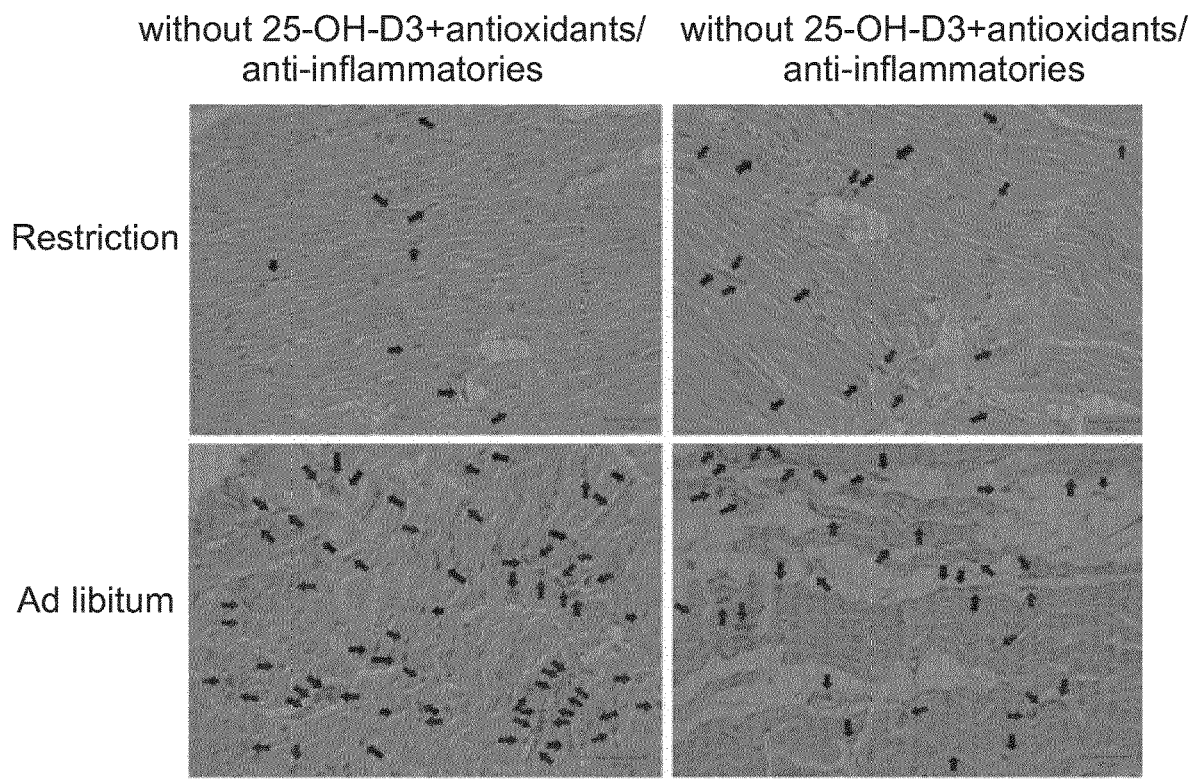
FIG. 16 are photos showing the effect of dietary supplementation of 25-OH-D3+antioxidants/anti-inflammatories on cardiac cell apoptosis of broiler hens with restricted or ad libitum feed intake. (at age of 35 weeks)
Figure 16:
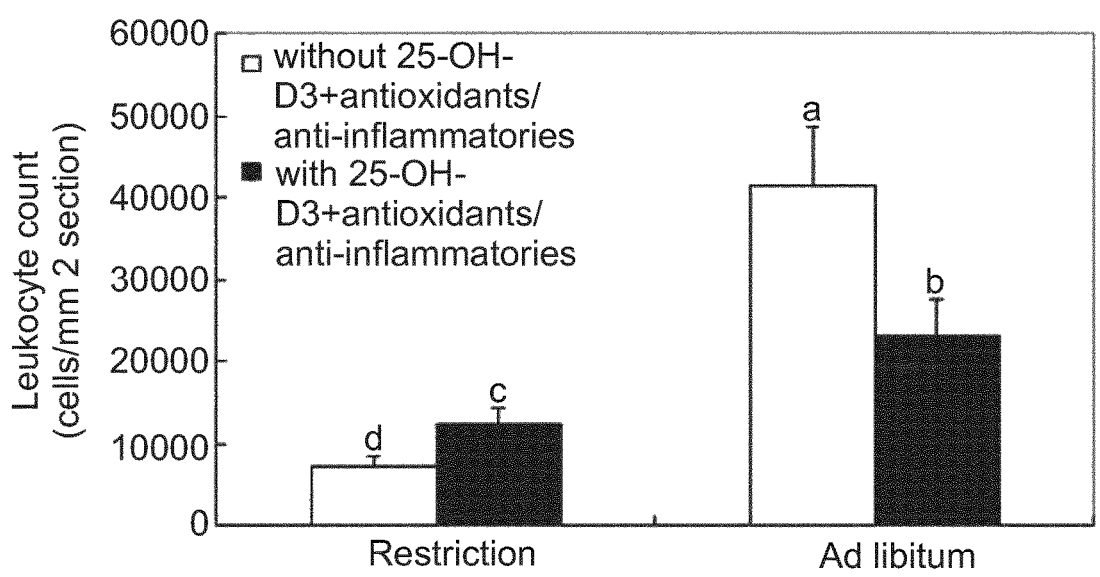
Figure 17:
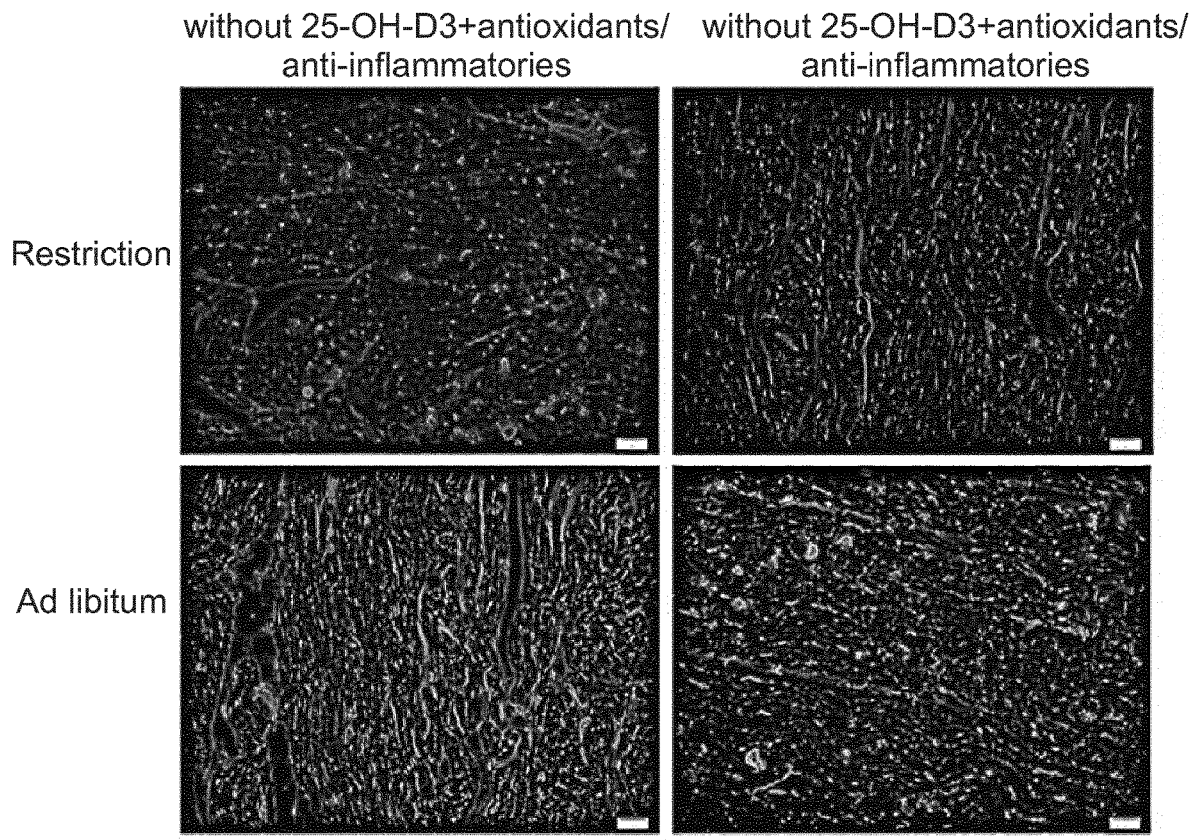
Figure 17:
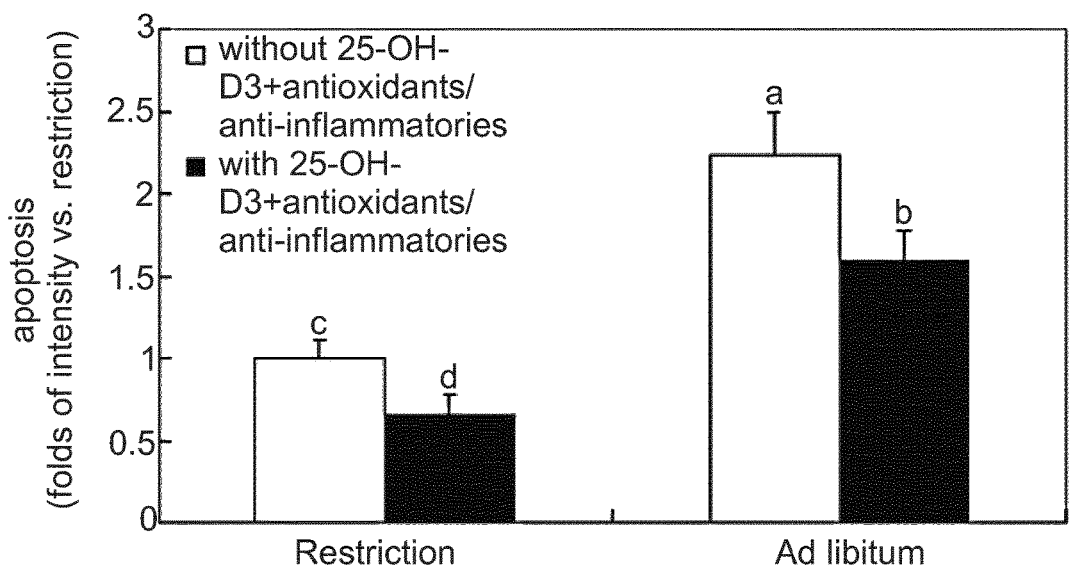

Conclusions and Annotations from FIG. 16
  25-OH-D3+antioxidants/anti-inflammatories ameliorated cardiac cell apoptosis in hens with restricted or ad libitum feed intake.

CONCLUSIONS

Use of supplemental 25-OH D3 and antioxidants/anti-inflammatories ameliorated deleterious effects associated has various cardiovascular benefits. Thus this invention includes use of 25-OH D3 and antioxidants/anti-inflammatories for at least one cardiovascular benefit selected from the group consisting of:

a) clearance of non-esterified fatty acids;
b) amelioration of plasma dyslipidemia (triglycerides, sphingomyelin, and ceramide);
c) amelioration of triglyceride and ceraminde accumulation in the liver, leg, breast muscle, and heart;
d) suppression of the tissue pro-inflammatory IL-1β production and plasma IL-6 concentration;
e) cardiac protection and enhanced cardiac function through the up-regulation of the phosphorylation of STAT-3 (signal transducer and activator of transcription 3) in the heart;
f) suppression of the infiltration of immune cells into the heart;
g) decreasing the incidence of ascites;
h) decreasing the incidence of sudden death in the flock due to cardiovascular problems;
i) decreasing the incidence of cardiac morbidities (dilation, pericardial effusion, rupture);
j) decreasing the amount of irregular incidence of ECG patterns;
k) decreasing the occurrence of arrhythmias;
l) ameliorating cardiac fibrosis;
m) ameliorating chronic systemic inflammation; and
n) ameliorating cardiac cell apoptosis in hens with restricted or ad libitum feed intake.

What is claimed is:

1. A method of controlling obesity in vitamin replete poultry and/or providing a cardiovascular benefit to vitamin replete poultry comprising administering a composition comprising a combination of 25-hydroxy vitamin D, canthaxanthin, Vitamin E and Vitamin C to the vitamin replete poultry which are fed ad libitum, and wherein the cardiovascular benefit is at least one benefit selected from the group consisting of:

a) clearance of non-esterified fatty acids;
b) amelioration of plasma dyslipidemia;
c) amelioration of triglyceride and ceraminde accumulation in the liver, leg, breast muscle, and heart;
d) suppression of a tissue pro-inflammatory IL-1β production and plasma IL-6 concentration;
e) cardiac protection and enhanced cardiac function through an up-regulation of phosphorylation of STAT-3 in the heart;
f) suppression of an infiltration of immune cells into the heart;
g) decreasing an incidence of ascites;
h) decreasing an incidence of sudden death in a flock due to cardiovascular problems;
i) decreasing an incidence of cardiac morbidities selected from the group consisting of dilation, pericardial effusion, and rupture;
j) decreasing an amount of irregular incidence of ECG patterns;
k) decreasing an occurrence of arrhythmias;
l) ameliorating cardiac fibrosis;
m) ameliorating chronic systemic inflammation; and
n) ameliorating cardiac cell apoptosis.

2. The method according to claim 1, additionally comprising administering at least one further bio-active ingredient selected from the group consisting of: Vitamin D, Vitamin B2, Vitamin B6, Niacin, Pantothenic Acid, Folic Acid, Biotin, Zinc, Copper, Manganese, Selenium, and combinations thereof.

* * * * *